(12) United States Patent
Arcenio et al.

(10) Patent No.: US 8,795,365 B2
(45) Date of Patent: Aug. 5, 2014

(54) EXPANDABLE DEVICES FOR EMPLACEMENT IN BODY PARTS AND METHODS ASSOCIATED THEREWITH

(75) Inventors: Gregory B. Arcenio, Redwood City, CA (US); Christopher U. Phan, San Leandro, CA (US)

(73) Assignee: Warsaw Orthopedic, Inc, Warsaw, IN (US)

( * ) Notice: Subject to any disclaimer, the term of this patent is extended or adjusted under 35 U.S.C. 154(b) by 1241 days.

(21) Appl. No.: 12/054,226

(22) Filed: Mar. 24, 2008

(65) Prior Publication Data
US 2009/0240335 A1     Sep. 24, 2009

(51) Int. Cl.
*A61F 2/44* (2006.01)

(52) U.S. Cl.
USPC ........................................ 623/17.11

(58) Field of Classification Search
USPC ................... 623/17.11, 17.15, 17.16
See application file for complete search history.

(56) References Cited

U.S. PATENT DOCUMENTS

| | | | |
|---|---|---|---|
| 4,083,369 A | 4/1978 | Sinnreich | |
| 4,313,434 A | 2/1982 | Segal | |
| 4,327,736 A | 5/1982 | Inoue | |
| 4,422,451 A | 12/1983 | Kalamchi | |
| 4,904,257 A | 2/1990 | Mori et al. | |
| 4,969,888 A | 11/1990 | Scholten et al. | |
| 5,026,373 A | 6/1991 | Ray et al. | |
| 5,108,404 A | 4/1992 | Scholten et al. | |
| 5,254,091 A | 10/1993 | Aliahmad | |
| 5,439,447 A | 8/1995 | Miraki | |
| 5,702,395 A | 12/1997 | Hopf | |
| 5,749,916 A | 5/1998 | Richelsoph | |
| 5,976,187 A | 11/1999 | Richelsoph | |
| 6,080,155 A | 6/2000 | Michelson | |
| 6,102,950 A | 8/2000 | Vaccaro | |
| 6,126,689 A | 10/2000 | Brett | |
| 6,129,763 A | 10/2000 | Chauvin et al. | |
| 6,203,574 B1 | 3/2001 | Kawamura | |
| 6,241,734 B1 | 6/2001 | Scribner et al. | |
| 6,290,724 B1 | 9/2001 | Marino | |
| 6,387,130 B1 * | 5/2002 | Stone et al. | ................. 623/17.16 |
| 6,409,766 B1 | 6/2002 | Brett | |

(Continued)

FOREIGN PATENT DOCUMENTS

| | | |
|---|---|---|
| EP | 1 532 949 B2 | 7/2007 |
| FR | 2900814 A | 11/2007 |

(Continued)

OTHER PUBLICATIONS

Jacob's Ladder. Retrieved form the internet: <URL:http://www.jamboree.freedom-in-education.co.uk/w's%20craft%20corner/jacob's%20ladder.htm.*

(Continued)

*Primary Examiner* — Bruce E Snow

(57) ABSTRACT

Disclosed are devices and methods for emplacement of an expandable device in a body part of interest in human and animal subjects. In one embodiment, the expandable device comprises a cage that may be emplaced in the intervertebral disc for use in spine fusion techniques. The device is fashioned so that it may be delivered to the intervertebral disc by percutaneous means, such as via a cannula. Additionally disclosed are systems and kits employing the devices of the invention as well as methods of manufacturing the devices of the invention.

19 Claims, 25 Drawing Sheets

(56) References Cited

U.S. PATENT DOCUMENTS

| | | |
|---|---|---|
| 6,419,705 B1 | 7/2002 | Erickson |
| 6,423,083 B2 | 7/2002 | Reiley et al. |
| 6,436,140 B1 | 8/2002 | Liu et al. |
| 6,443,989 B1 | 9/2002 | Jackson |
| 6,491,695 B1 | 12/2002 | Roggenbuck |
| 6,579,532 B1 | 6/2003 | Mandel et al. |
| 6,582,467 B1 | 6/2003 | Teitelbaum et al. |
| 6,652,533 B2 | 11/2003 | O'Neil |
| 6,695,760 B1 | 2/2004 | Winkler et al. |
| 6,740,093 B2 | 5/2004 | Hochschuler et al. |
| 6,749,613 B1 | 6/2004 | Conchy et al. |
| 6,764,515 B2 | 7/2004 | Ralph et al. |
| 6,773,460 B2 | 8/2004 | Jackson |
| 6,814,734 B2 | 11/2004 | Chappuis et al. |
| 6,821,298 B1 | 11/2004 | Jackson |
| 6,835,206 B2 | 12/2004 | Jackson |
| 6,893,464 B2 | 5/2005 | Kiester |
| 6,918,934 B2 | 7/2005 | Ralph et al. |
| 6,955,691 B2 | 10/2005 | Chae et al. |
| 7,011,658 B2 | 3/2006 | Young |
| 7,018,415 B1 | 3/2006 | McKay |
| 7,056,321 B2 | 6/2006 | Pagliuea et al. |
| 7,087,055 B2 | 8/2006 | Lim et al. |
| 7,118,598 B2 | 10/2006 | Michelson |
| 7,128,760 B2 | 10/2006 | Michelson |
| 7,141,070 B2 | 11/2006 | Ralph et al. |
| 7,153,281 B2 | 12/2006 | Holmes |
| 7,179,225 B2 | 2/2007 | Shluzas et al. |
| 7,217,293 B2 | 5/2007 | Branch, Jr. |
| 7,226,451 B2 | 6/2007 | Shluzas et al. |
| 7,226,482 B2 | 6/2007 | Messerli et al. |
| 7,285,135 B2 | 10/2007 | McKay et al. |
| 7,291,152 B2 | 11/2007 | Abdou |
| 7,303,584 B2 | 12/2007 | Castro et al. |
| 2002/0111686 A1 | 8/2002 | Ralph et al. |
| 2004/0034422 A1 | 2/2004 | Errico et al. |
| 2004/0093088 A1 | 5/2004 | Ralph et al. |
| 2004/0106997 A1 | 6/2004 | Lieberson |
| 2004/0147928 A1 | 7/2004 | Landry et al. |
| 2004/0167625 A1 | 8/2004 | Beyar et al. |
| 2004/0249382 A1 | 12/2004 | Olson, Jr. et al. |
| 2004/0249466 A1 | 12/2004 | Liu et al. |
| 2004/0254643 A1 | 12/2004 | Jackson |
| 2005/0070911 A1 | 3/2005 | Carrison et al. |
| 2005/0080489 A1 | 4/2005 | Estes et al. |
| 2005/0136038 A1 | 6/2005 | de Bruijn |
| 2005/0182491 A1 | 8/2005 | Ralph et al. |
| 2005/0234554 A1 | 10/2005 | Ralph et al. |
| 2006/0041258 A1 | 2/2006 | Galea |
| 2006/0122701 A1 | 6/2006 | Kiester |
| 2006/0142858 A1 | 6/2006 | Colleran et al. |
| 2006/0189999 A1* | 8/2006 | Zwirkoski ............ 606/90 |
| 2006/0206207 A1 | 9/2006 | Dryer et al. |
| 2006/0212118 A1 | 9/2006 | Abernathie |
| 2006/0264935 A1 | 11/2006 | White |
| 2006/0287725 A1 | 12/2006 | Miller |
| 2007/0043442 A1 | 2/2007 | Abernathie et al. |
| 2007/0067035 A1 | 3/2007 | Falahee |
| 2007/0093897 A1 | 4/2007 | Gerbee et al. |
| 2007/0118171 A1 | 5/2007 | Reiley et al. |
| 2007/0219634 A1 | 9/2007 | Greenhalgh et al. |
| 2007/0270951 A1 | 11/2007 | Davis et al. |
| 2007/0282443 A1 | 12/2007 | Globerman et al. |
| 2008/0125865 A1* | 5/2008 | Abdelgany ............ 623/17.16 |

FOREIGN PATENT DOCUMENTS

| | | |
|---|---|---|
| JP | 8038618 | 2/1996 |
| WO | 9856301 | 12/1998 |
| WO | WO 2007/022021 A1 | 2/2007 |
| WO | WO 2007/131026 A2 | 11/2007 |

OTHER PUBLICATIONS

Folman et al., "Posterior Lumbar Interbody Fusion for Degenerative Disc Disease Using a Minimally Invasive B-Twin Expandable Spinal Spacer," Journal of Spinal Disorders & Techniques, 2003, 16(5): 455-460.

Dickman, M.D. et al., "Fixation and Fusion of the Lumbar Spine Using Threaded Interbody Cages." *BNI Quarterly*, 1997, 13(3) 4-25.

* cited by examiner

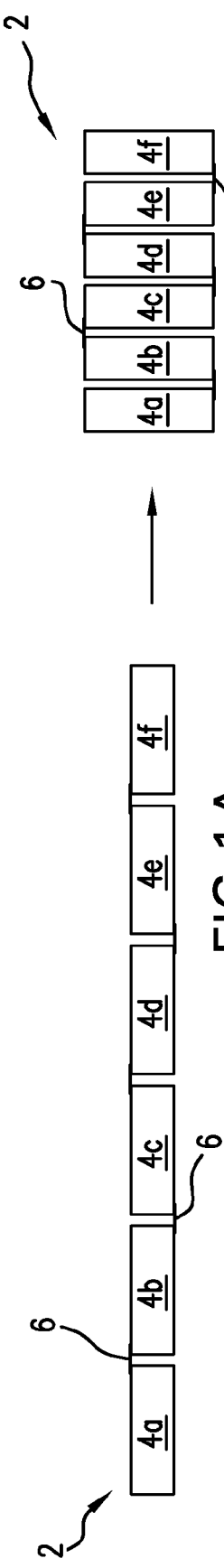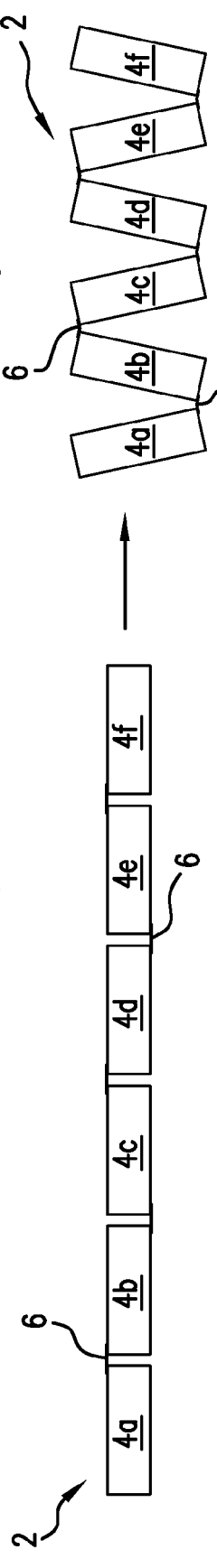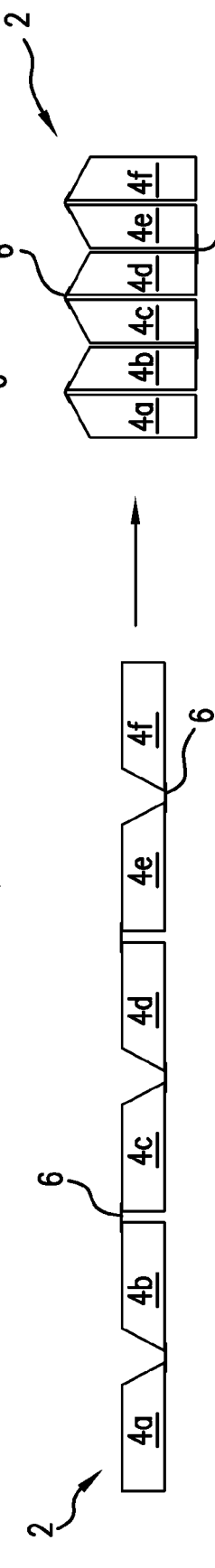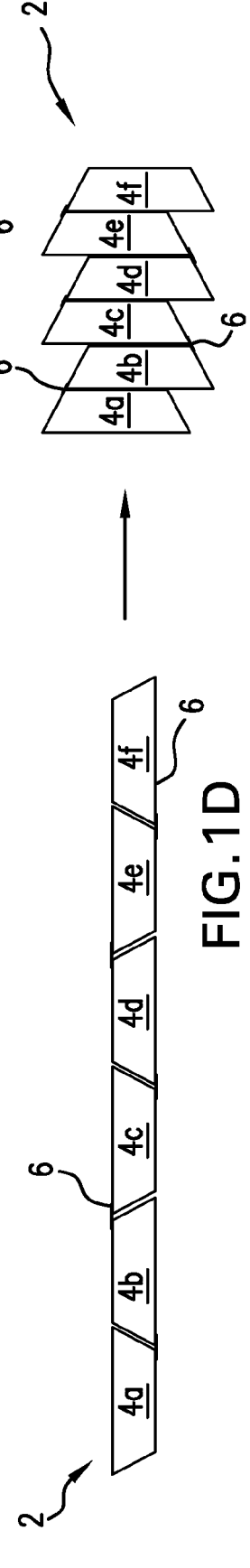

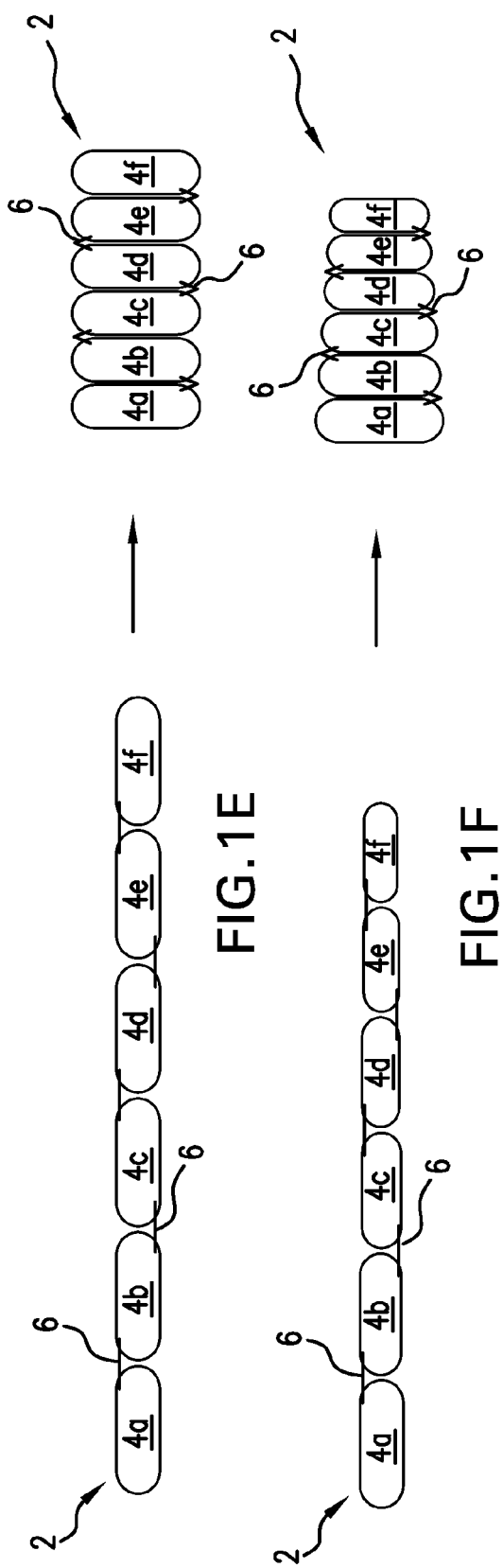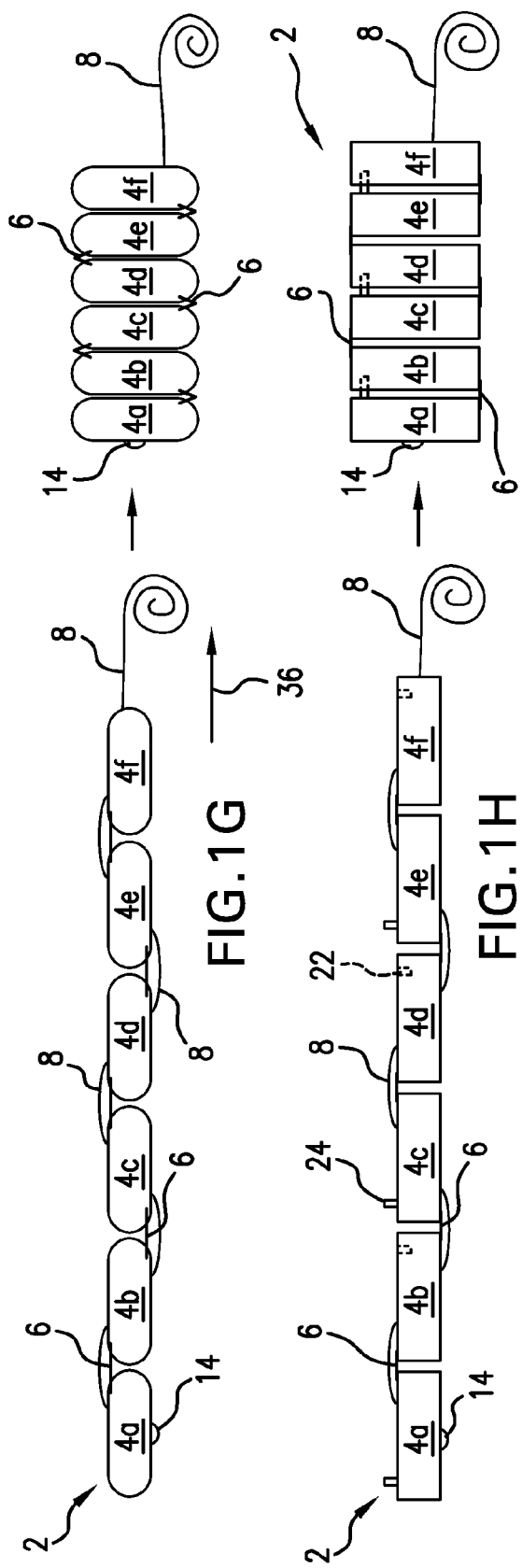

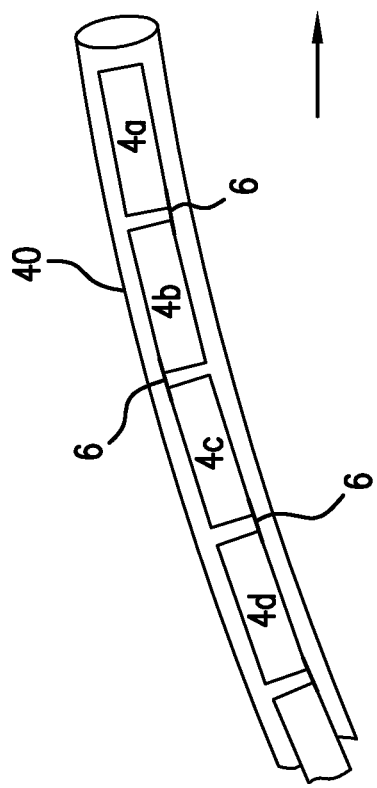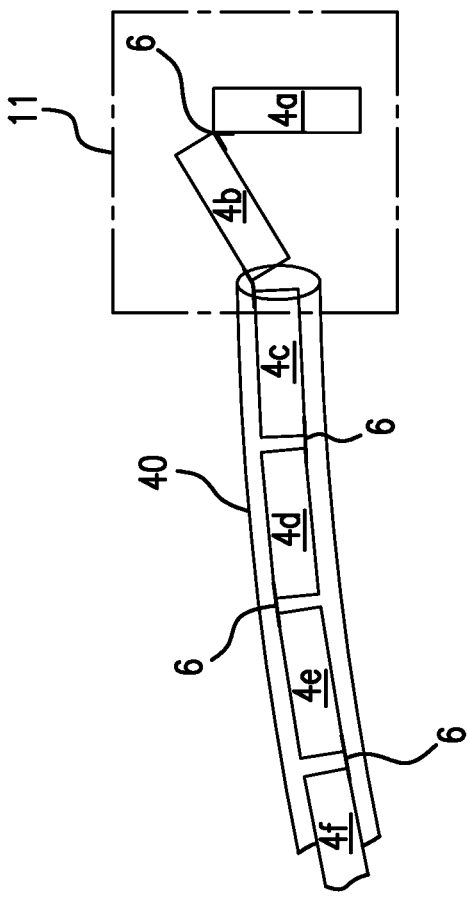
FIG.1I

EXPANDABLE DEVICES FOR EMPLACEMENT IN BODY PARTS AND METHODS ASSOCIATED THEREWITH

FIELD OF THE INVENTION

The present invention relates to expandable devices, such as fusion cages, for emplacement in body parts and methods associated therewith.

BACKGROUND OF THE INVENTION

Prosthetic devices may be used to repair a variety of body parts. For example, expandable devices such as fusion cages may provide a stabilized opening for inserting a bone graft between adjacent portions of bone. In time, the bone and bone graft can grow together through or around the fusion cage to fuse the graft and the bone solidly together. Current uses of fusion cages include treating a variety of spinal disorders, including degenerative disc diseases, Grade I or II spondylolistheses, adult scoliosis and other disorders of the lumbar spine. Spinal fusion cages are often inserted into the intervertebral disc space between two vertebrae for fusing them together. Such fusion cages can distract or expand a collapsed disc space between two vertebrae to stabilize the vertebrae by preventing the vertebrae from moving relative to each other.

A typical fusion cage is generally cylindrical, hollow, and threaded. Alternatively, some fusion cages are unthreaded or made in tapered, elliptical, or rectangular shapes. Known fusion cages are generally constructed from a variety of materials including titanium alloys, porous tantalum, other metals, allograft bone, carbon fiber or ceramic material.

Fusion cages may be used to connect any adjacent portions of bone or other solid body parts. However, one standard use of fusion cages is in the spine. Although often used in the lumbar spine, fusion cages can also be used in the cervical or thoracic spine. Fusion cages can be inserted in the spine using an anterior, posterior, or lateral approach. Insertion is usually accomplished through a traditional open surgery which can be traumatic to the patient and require weeks, if not months, of recovery.

General techniques for inserting fusion cages are known. For example, insertion techniques and details on the design of fusions is described in Internal Fixation and Fusion of the Lumbar Spine Using Threaded Interbody Cages, by Curtis A. Dickman, M. D., published in BNI Quarterly, Volume 13, No. 3, 1997, which is hereby incorporated by reference. For example, many threaded fusion cages are inserted by first opening the disc space between two vertebrae of the lumbar spine using a wedge or other device on a first side of the vertebrae. Next, a tapered plug may be inserted into the spine at the site of the disc that is being replaced with the expandable device. The plug may be used to hold the disc space open in the case of a threaded, cylindrical cage insert. A threaded opening may then be then drilled and tapped on a second side of the spine that is opposite the side used for accessing the first plug. This double access thereby produces the equivalent of a "split" threaded bore defined by the walls of the vertebrae above and below the bore. The threaded expandable device may then be threaded into the bore and the wedge removed. The first side may then be drilled and tapped before inserting a second threaded expandable device. Typically, two threaded expandable devices are used at each intervertebral disc level.

Traditionally, back surgery to insert a fusion cage has been done using an incision that was larger than the part being delivered to the spine. In this way, surgeons were able to deliver medical devices to the desired site without undue concern regarding the size of the medical device. However, with the development of small incision techniques such as arthroscopic surgery and/or kyphoplasty, it is generally preferred to be able to deliver medical devices through smaller incisions. The ability to perform the surgery with a smaller incision ultimately results in faster healing times for patients. In some instances, it is desired to be able to deliver one or more medical device(s) through a cannula. However, as the cannula generally has a small diameter, such devices may need to be expanded to a larger state to perform the role required.

Thus, it would be beneficial to provide an expandable device that can be delivered percutaneously (e.g., via a cannula) to the body part of interest and then expanded in situ. The expandable device could also be designed to allow the expandable device to be expanded in the body part of interest while minimizing trauma to the adjacent tissue. Such expandable devices would be useful for repair of the spine or other body parts.

BRIEF SUMMARY OF THE INVENTION

In certain embodiments, the present invention comprises devices and methods for emplacing an expandable device in a body part of interest. In one embodiment, the present invention comprises expandable device for emplacing in a body part in a subject, where the device comprises a plurality of segments, the plurality of segments being flexibly connected in series, the expandable device having a first configuration wherein the plurality of segments are substantially unfolded, and a second configuration wherein the plurality of segments are substantially folded, and wherein a total height of the expandable device in the second configuration is substantially spanned by at least one of the plurality of segments.

In some embodiments, the devices and methods are used to implant intervertebral expandable device. Such expandable devices may be expanded between two adjacent vertebrae to cause the vertebrae to change position relative to each other and/or produce a normal alignment of the spine. Alternatively or additionally, the expandable device may provide a support that can be filled in with bone graft material to thereby result in fusion of the vertebrae. For example, in some embodiments, the expandable device of the present invention may comprise a fusion cage used in spinal fusion procedures.

In certain embodiments, the invention relates to an expandable device that may be inserted into an intervertebral space by percutaneous access. For example, the expandable device may be inserted via a cannula. In certain embodiments, the expandable device expands as it exits the cannula. The expandable device may thus expand in situ, to provide a means to support the two adjacent vertebral bodies. In yet other embodiments, a biological bone graft and/or other matrix material is emplaced within any voids that remain between the two vertebral bodies after the cage or cages of the invention are emplaced. For example, in some embodiments, the expandable device of the present invention may comprise a fusion cage that is delivered by percutaneous access.

Other embodiments and further details on various aspects of the present invention are set forth in the following description, figures, and claims. It is to be understood that the invention is not limited in its application to the details set forth in the following description, figures, and claims, but is capable of other embodiments and of being practiced or carried out in various ways.

BRIEF DESCRIPTION OF THE DRAWINGS

FIG. 1 shows various alternate expandable devices having different features or being used with a cannula as Panels 1A-1I in accordance with alternate embodiments of the present invention.

DETAILED DESCRIPTION OF THE INVENTION

Figure 2:
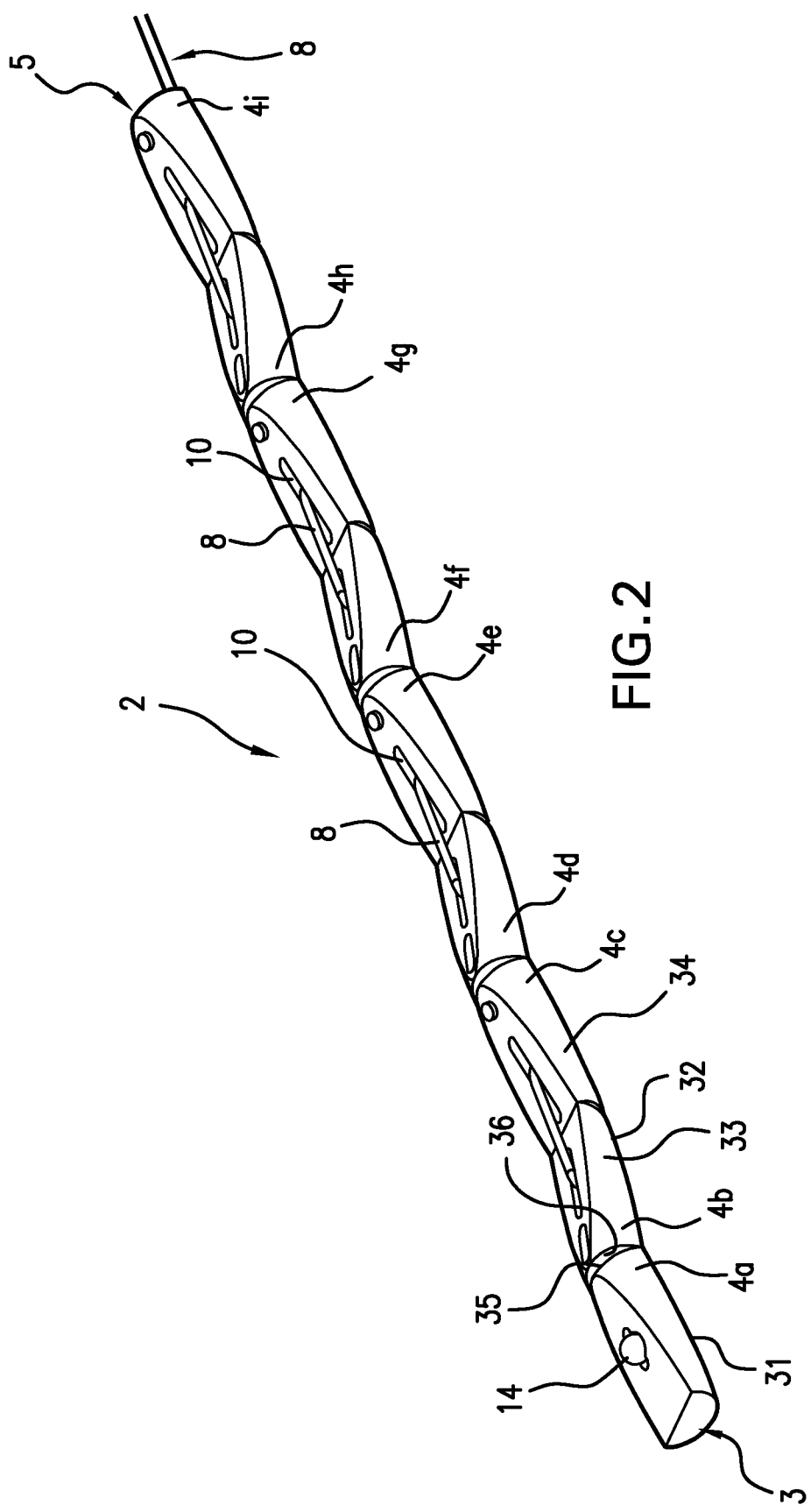
FIG. 2 shows a perspective view of an expandable device in an undeployed state in accordance with one embodiment of the present invention.

Unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

Also, where ranges are provided, it is understood that other embodiments within the specified ranges are to be included.

As used herein, a subject is an animal. For example, the subject may comprise a mammal. In one embodiment, the subject may be a human. The user of the products, methods, and systems of the present invention may be a physician, veterinarian, a health care professional, or another person or device.

As used herein, an internal body part may comprise a bone, bony tissue (e.g., spinal tissue), or bones or part of a bone. The body part may comprise a portion of a spine, such as a vertebral body, an intervertebral spinal disc, or an intervertebral region. For example, due to various traumatic or pathologic conditions, such as cancer, a vertebral body or an intervertebral disc can experience fracture, degradation of the tissue, or expansion, and the like, that can lead to compression of the nerves, a reduction in mobility, and discomfort. The present invention is not, however, limited in application to bones, discs, or vertebrae, and may be used to repair other parts of a living or non-living organism. For example, in certain embodiments, the devices, methods, and systems or kits of the present invention can be deployed in other bones or other tissue types, such as an arm bone, a leg bone, an organ (e.g., organs needing emplacement of structures that may be expanded in situ), a portion of the vasculature, cartilage or tendons requiring surgical access and repair (e.g., a joint), and other body parts.

As used herein, an expandable device is a device that is emplaced within a body part or between adjacent body parts and expanded in at least one dimension. In certain embodiments, the expandable device may be a fusion cage that functions to provide support for two body parts such that fusion of the body parts may be performed. For example, in certain embodiments, a fusion cage may be used to fuse two vertebral bodies together, as for example, when the disc between the two vertebral bodies has disintegrated. This is known as a spinal fusion.

As used herein, an access path is an incision made in a subject to access an internal body part. In an embodiment, a percutaneous access is used. As used herein, a percutaneous access is a procedure whereby access to an inner organ or tissue is done via needle puncture of the skin, rather than using an "open" approach where the inner organs or tissue are exposed (e.g., such as surgery or cutting the skin with a scalpel). In one embodiment, the access path is made using an access member. For example, a percutaneous surgical access denotes passage through substantially unbroken skin, as for example, by needle puncture, a cannula or a catheter.

Also, as used herein, an access member comprises a device for accessing a predetermined location or body part in a subject. The inner volume of the access member may provide a path to access a region or a body part that is located within the subject's body. The access member may be any type of device that can extend from the location of interest (e.g., a bone or an organ) to be accessible to a user of the access member. For example, the access member may be designed to extend from an internal body part (e.g., a spine or other type of bone) in a subject to outside of the subject's body. As described in more detail herein, the access member may be an elongated hollow member such as a hollow cylinder, a tube, a cannula or a catheter.

Also, as used herein, a material for emplacement within, or delivery to, a body part in a subject may comprise any material that is biologically compatible with the body part of interest. For example, in alternate embodiments, the material may comprise a bone filler material or an adhesive. As used herein, a bone filler material comprises any material that may be used for the treatment of bone. A variety of materials have been described for use as bone filler materials (see e.g., U.S. Pat. Nos. 4,904,257, 6,203,574, 6,579,532, 6,740,093, and Patent Application No. 2005/0136038 for descriptions of bone filler materials). In one embodiment, the bone filler or treatment material may comprise PMMA. Alternatively, the bone filler material may comprise a cement, a gel, a fluid, or an adhesive, such as materials that are commercially available for repair of the spine and other bones or boney tissues. In other embodiments the bone graft material of the present invention may include allograft, autograft, BMP (bone-morphogenic proteins), bone marrow aspirate, demineralized bone matrix, ceramics, calcium phosphates, blood platelet gels, and other similar and known materials.

As used herein, the words "anterior" and "posterior" refer to the front and back of the subject, respectively. In addition, the words "proximal" and "distal" refer to directions closer to, and away from, respectively, an operator or user (e.g., surgeon, physician, nurse, technician, veterinarian, etc.) who would insert the expandable device of the present invention into a subject (e.g., patient), with the tip-end (i.e., distal end) of the device inserted inside a subject's body. Thus, for example, the end of the access member inserted inside the subject's body would be the distal end of the access member, while the end of the access member outside the subject's body would be the proximal end of the access member. Also as used herein, the terms "upper" and "lower" are used to describe one embodiment of how the device may be viewed, and as such, the terms may be interchangeable.

Also, as used herein the term "axial end" or "axial surface" refers to the end that is perpendicular to the longitudinal axis of a segment of the expandable device of the present invention. The term "longitudinal surface" denotes a surface that is parallel to the longitudinal axis of a segment of the expandable device of the present invention. The longitudinal axis refers to the axis that is parallel to the longest dimension of a segment of the expandable device of the present invention.

As used herein, a bilateral access is such that the body part is accessed from both sides of a midline along at least one plane (e.g., the x-y plane or the x-z plane).

As used herein, a segment is a portion of a whole part. Segments may be the same size and shape, or segments may be different sizes and shapes. The segments may be connected to each other or the segments may not be connected to each other.

As used herein, the term "substantially folded" refers to a configuration where two adjacent parts are in a configuration such that the two parts are rotated around an axis that is adjacent to at least one end of each part, and where in the substantially folded configuration, the angle between the two parts is reduced as compared to a configuration where the two parts are unfolded.

As used herein, the term "substantially unfolded" refers to a configuration where two adjacent parts are in a configuration such that the two parts are rotated around an axis that is adjacent to at least one end of each part, and where in the substantially unfolded configuration, the angle between the two parts is increased as compared to a configuration where the two parts are substantially folded.

As used herein, the term "span" means to extend over the entire length.

As used herein, folded in alternating directions indicates that there are at least two adjacent folds that are not in the same direction. Examples of being folded in alternating directions are three connected parts that are folded as a Z shape, or four connected parts that are folded as a W shape, or multiple connected parts that are folded as an accordion shape. The parts may be parallel or not parallel in the final folded shape. As used herein, two connected parts that are folded in one direction can assume a V shape.

As used herein, a living hinge is a hinge or flexure bearing with no moving parts. Living hinges are often thin sections of a material that can bend to allow movement.

Also as used herein, an elongated member is a member that is substantially longer in length than in diameter or circumference. Examples of elongated members are cannulas, stylets and wires.

Foldable Expandable Devices

In certain embodiments, the present invention relates to expandable devices and methods, systems and kits associated therewith. The expandable devices may be used to facilitate stabilization and/or fusion of two adjacent body parts. Thus, in certain embodiments, the expandable devices are fusion cages. In certain embodiments, the expandable devices are designed for percutaneous delivery. For example, in certain embodiments, the present invention relates to devices, methods, systems and/or kits for implanting an intervertebral expandable device that can be selectively expanded between two adjacent vertebrae to cause the vertebrae to maintain position relative to each other so as to produce a normal alignment of the spine, while promoting fusion of the vertebrae.

For example, the products, methods, kits and systems of the present invention may be used to repair an intervertebral disc as when degeneration of the disc occurs. Or, due to various traumatic or pathologic conditions, such as osteoporosis, a vertebral body can experience a vertebral compression fracture (VCF). In such conditions, at least a part of the vertebral bone can be compacted, causing a decrease in height of the vertebra. In many cases, vertebral height is lost in the anterior region of the vertebral body. Thus, the devices, methods, kits and systems of the present invention may by used to repair a vertebral body lost due to a fracture, or when other degeneration occurs. The present invention is not limited in application to spinal discs and vertebrae, and may be used to repair other parts of a living or non-living organism. For example, in embodiments, the products, methods, kits and/or systems of the present invention can be deployed in other body parts such as other types of bones, joints, or organs.

For example, in one embodiment, the present invention comprises an expandable device for emplacing in a body part in a subject, wherein the device comprises: a plurality of segments, the plurality of segments being flexibly connected in series, the expandable device having a first configuration wherein the plurality of segments are substantially unfolded, and a second configuration wherein the plurality of segments are substantially folded, and wherein a total height of the expandable device in the second configuration is substantially spanned by at least one of the plurality of segments.

In one embodiment, the plurality of segments is folded in alternating directions in the second configuration. For example, in one embodiment, the present invention comprises an expandable device for emplacing in a body part in a subject comprising: a plurality of connected segments, the plurality of connected segments having a first configuration wherein a plurality of longitudinal axes of the plurality of connected segments are substantially coaxial, and a second configuration wherein the plurality of connected segments are folded in alternating directions.

FIG. 1A-1F show various embodiments of devices of the present invention. Thus, shown in FIG. 1A-1F are expandable devices 2 having segments (e.g., 4a-4f) that are flexibly connected at part 6. It can be seen that the segments may comprise a variety of shapes and sizes. Thus, in alternating embodiments, the segments may be rectangular or cylindrical (e.g., FIG. 1A and FIG. 1B). Alternatively, the segments may be a polygon such as a trapezoid (e.g., FIG. 1C or 1D). In this way, with the device assumes the second configuration, at least a portion of the device may comprise protrusions that can impinge upon the surface of the body part into which the device is emplaced and/or expanded. In yet other embodiments, the segments may be rounded (e.g., having an oval cross-section) (FIG. 1E and FIG. 1F).

The segments may each be the same size and shape, or the segments may be different sizes and/or shapes (FIG. 1F). For example, as shown in FIG. 1F, different sized segments may be appropriate where the body part into which the device is inserted does not have parallel surfaces.

The device can assume a first configuration in which the plurality of segments are substantially unfolded (see left side of each of FIGS. 1A-1F) or a second configuration in which the plurality of the segments are substantially folded (see right side of each of FIGS. 1A-1F). In one embodiment, the plurality of longitudinal axes of the plurality of connected segments are substantially co-axial in the first configuration. Thus, as shown in FIGS. 1A-1F, the device may have a first configuration such that the individual segments are substantially end to end. Also in one embodiment, the plurality of longitudinal axes of the plurality of connected segments are substantially parallel in the second configuration. This configuration is illustrated in FIGS. 1A and 1C-1F. For example, in one embodiment, a longitudinal surface of a first one of the plurality of connected segments is substantially flush with a longitudinal surface of a second one of the plurality of connected segments in the second configuration. Thus, the device may comprise a first member comprising a plurality of segments that may fold in a coordinated manner from a first configuration in which the segments are aligned such that an axial end of each segment is substantially flush with an axial end of an adjacent segment, to a second configuration wherein a longitudinal surface of at least one segment is substantially flush with a longitudinal surface of a second, adjacent segment. Or, the plurality of longitudinal axes of the plurality of connected segments may be generally non-parallel in the second configuration as is shown in one embodiment in FIG. 1B.

The segments may be separate parts, or the segments may be joined together as a single unit. In one embodiment, the plurality of connected segments are connected by a plurality of hinges, each of the plurality of hinges having a thickness less than a thickness of each of the plurality of connected segments. Such hinges 6 are shown in FIG. 1 for a variety of expandable devices. In one embodiment, the segments are each connected to at least one other of the plurality of segments. For example, in one embodiment the segments (e.g., 4a-4f) are connected to each other by a hinge 6 between adjacent segments. A variety of hinges may be used. In some embodiments, the plurality of connected segments are connected by living hinges.

In some embodiments, the device can include hinges and/or elastic structures (e.g., elastic strings/bands or springs) that bias the segments towards a substantially folded configuration (i.e., the second configuration). Thus, in some embodiments, the hinge is connected between at least two of the plurality of segments for biasing the plurality of segments towards the second configuration. For example, each hinge 6 could have a naturally folded state, thereby causing segments 4a-4f, and by extension, device 2, to exhibit a "default" folded configuration. Emplacement of device in a target body part could then involve restraining the device in its substantially unfolded configuration (i.e., the first configuration) by placing it within a cannula, and then urging device from the cannula into the target body part. Upon exiting the cannula, the device would then automatically expand into its substantially folded configuration.

In other embodiments, the device comprises a repositioning member for urging the segments between the first configuration and the second configuration. Embodiments of such a device are shown schematically in FIGS. 1G and 1H. For example, the device may comprise a repositioning member 8 for urging the segments from the first configuration to the second configuration. In one embodiment, the repositioning member engages each of the segments. In this way, the repositioning member can be used by an operator of the device to urge the segments from the first configuration to the second configuration, or from the second configuration to the first configuration. In one embodiment, the repositioning member can be loosened to allow the segments to assume the first configuration (e.g., substantially unfolded) or tightened to urge the segments to assume the second configuration (e.g., substantially folded). Thus, in one embodiment, the present invention comprises an expandable device for emplacing in a body part in a subject comprising a plurality of segments, and a repositioning member that engages each of the segments, wherein the repositioning member can be loosened to allow the segments to be positioned such that the axial end of one segment is substantially flush with an axial end of an adjacent segment, or the repositioning member can be tightened (e.g., by pulling along axis 30 as shown in FIGS. 1G and 1H) such that a longitudinal surface of one segment is substantially flush with a longitudinal surface of a second segment.

In other embodiments, repositioning member 8 can be an elastic member connected between at least two of segments 4a-4i for pulling the segments towards each other. For example, repositioning member 8 could be fixedly connected to segments 4a (via attachment element 14) and 4f (via an attachment element substantially similar to attachment element 14). Note that in such a construction, member 8 would not need to extend beyond segment 4f as depicted in FIG. 1. By providing a force drawing segments 4a and 4i together, elastic member 8 would bias device 2 towards its expanded (i.e., substantially folded) configuration.

In some embodiments, the repositioning member comprises a wire that is passed through at least one aperture on each of the segments. The wire may pass through the segments in an alternating manner. For example, the wire may loop through an aperture positioned in each of the segments in a manner so as to extend from a first segment to a second segment on one face of the unit (e.g., upper or superior) and then to extend from the second segment to the third segment on the opposite face of the unit (e.g., lower or inferior). The wire may then extend from the third segment to the fourth segment on the superior face, and from the fourth segment to the fifth segment on the inferior face, and so forth, until all of the segments are connected.

The positioning of the wire relative to the upper and lower faces of the unit may allow for the wire to function so as to collapse the upper and lower faces (i.e., longitudinal surfaces) of the segments together such that the longitudinal surfaces of adjacent segments go from a substantially linear arrangement, to an arrangement where the longitudinal surfaces of adjacent segments are pulled together. Thus, in one embodiment, the wire may be fixedly attached 14 (FIG. 1H) to a segment positioned on one end of the device such that the when the wire is pulled toward the other segments, the adjacent segments are pulled towards each other such that the longitudinal surface of one segment is urged to a final configuration in which it is substantially flush with the longitudinal surface of a second segment. In one embodiment, the wire may be pulled such that it is completely tightened (i.e., can be pulled no further). At this point, the device will assume the second configuration such that the segments are substantially folded (see FIGS. 1G and 1H, where the device goes from a first configuration (left side of figure) to a second configuration (right side of figure) by pulling wire away from 14). As the longitudinal surface is longer than the axial surface, when the expandable device is deployed (i.e., folded) by pulling the wire, vertical expansion occurs.

Alternatively, the device may be deployed without the use of a repositioning member. In one embodiment, axial compression may be used to induce folding of the device. In such an embodiment, the distal end of the device may be pushed against a non-movable support (e.g., such as any remaining anterior wall of an intervertebral disc). By pushing the device against such a wall (or by delivering subsequent segments out of a cannula and into an intervertebral region as discussed in detail below), and simultaneously axially compressing the segments that are not constrained, the unconstrained segments (e.g., the segments that have exited the cannula) may be induced to pivot at their common hinge, to result in folding of the device and vertical expansion. In this way, axial compression may replace the use of a repositioning member.

In one embodiment, the expandable device, when fully deployed will have a height that is equal to the longitudinal length of each segment. In this way, vertical expansion will occur as the expandable device assumes a folded configuration. In certain embodiments, the segments may comprise elements to assist in the alignment of the segments in the second configuration, e.g., when the longitudinal surfaces of at least two segments are substantially flush. In this way, the tendency of the segments to twist off center and become misaligned can be reduced. For example, in one embodiment, the alignment elements may comprise at least one pin 24 (FIG. 1H) on a first segment and at least one aperture 22 (FIG. 1H) to receive the pin on an adjacent segment. Or, multiple pins and apertures may be used. Generally, each of the longitudinal surfaces may comprise at least two pins and receiving apertures. For example, in one embodiment, the pins and receiving apertures are positioned close to the axial end of each segment. In this way, when each pin and aperture interlock, the mating will prevent the two segments from twisting or wiggling relative to the longitudinal (i.e., longest) axis of the longitudinal surface.

In certain embodiments, an expandable device may be inserted into a body part via an access member. An embodiment of such a device is shown in FIG. 1I. In an embodiment, the access member may comprise a cannula 40. In some embodiments, the expandable device expands as it exits the cannula (i.e., right side of figure). The expandable device may thus expand in situ, e.g., inside body part 11, to provide a means to support the two adjacent vertebral bodies. In yet other embodiments, a biological bone graft or other matrix material may be emplaced within any voids that remain in the body part. For example, where the expandable device comprises a fusion cage emplaced between two vertebral bodies, a bone graft material may be emplaced in the remaining disc space.

In one embodiment, the segments are configured for percutaneous delivery to a body part using a cannula. In certain embodiments, the body part may comprise a spinal disc or an intervertebral region between two vertebral bodies. Thus, embodiments of the present invention may be used as expandable devices for insertion between two vertebral bodies during a spinal fusion procedure. Or, the expandable device may be used for emplacement in other body parts such as within a vertebral body or other bone structure during kyphoplasty or other repair procedures.

The present invention may be better understood by referring to additional non-limiting embodiments illustrated in the additional figures. For example, FIG. 2 shows one embodiment of the present invention comprising an expandable device for emplacement in a body part in a subject comprising a first member 2 comprising a plurality of segments 4a-4i that may fold in a coordinated manner from a first unfolded configuration to a second folded configuration. In one embodiment, the first configuration is such that the segments are substantially co-axial and the second configuration is such that a plurality of longitudinal surfaces are substantially parallel. For example, in one embodiment, the segments are aligned such that an axial end of each segment 35 is substantially flush with an axial end of an adjacent segment 36, to a second configuration wherein a longitudinal surface of at least one segment 31 is substantially flush with a longitudinal surface of a second, adjacent segment 32.

In some embodiments, the segments are each connected to at least one other of the plurality of segments. In an embodiment, the segments are connected by a living hinge. Also in some embodiments, the device comprises a repositioning member for urging the first member from the first substantially unfolded configuration to the second substantially folded configuration. The repositioning member may comprise a wire 8 that engages each of the segments. In some embodiments, the repositioning member can be loosened to allow the segments to assume the first unfolded configuration or tightened to urge the segments into the second folded configuration. In one embodiment, the repositioning member may be loosed to allow the segments to be positioned such that an axial end of each segment is substantially flush with an axial end of an adjacent segment, or the repositioning member can be tightened such that a longitudinal surface of at least one segment is substantially flush with a longitudinal surface of a second segment.

As noted above, in certain embodiments, the expandable device 2 is a structure having a plurality of interconnected segments (FIG. 2). Although the device shown in FIG. 2 has nine individual segments (i.e., 4a, 4b, 4c, 4d, 4e, 4f, 4g, 4h, and 4i) it will be understood that the number of segments may be varied as is required by the body part into which the expandable device will be inserted.

As shown in FIG. 2, in the undeployed or substantially unfolded state, the expandable device may be in its most extended form. It can be seen that the expandable device may be designed to be highly flexible along the bend axes of the individual living hinge pairs. Thus, as further illustrated in FIGS. 3 and 4, the individual segments may be connected at their longitudinal ends to adjacent segments through hinges 6 which are generated during the production of the expandable device. The hinges may be living hinges. The living hinges of the present invention can be made from any of a plurality of materials such as various polymers including, but not limited to, polypropylene or polyethylene, or mixtures thereof. In one embodiment, the segments and the hinge are made from the same material. For example, the expandable device of the present invention may comprise a single-piece, injection-molded part such that the hinges are made during the molding process. As described in more detail herein, the hinges may be very thin connectors between each of the segments so that upon deployment of the expandable device, the hinges are substantially flush with the upper and lower surfaces of the folded structure.

The expandable device may further include components to facilitate deployment. In one embodiment, deployment occurs in situ (i.e., at the body part where the cage is to be inserted). For example, in an embodiment, once the expandable device reaches the desired location in the intervertebral space for which treatment is required, deployment of the device may begin.

As noted herein, vertical expansion may be accomplished by tightening of a repositioning member (e.g., wire) that operably engages each of the segments. In one embodiment, the repositioning member 8 is fixedly fastened to the most distal segment and runs from the distal end of the device (e.g., the distal end of the most distal segment) 3 to the most proximal end of the device 5 (i.e., the most proximal end of the most proximal segment) (FIG. 2). In an embodiment, the repositioning member 8 is a wire.

The repositioning member may be made of any material that is biocompatible and of sufficient strength to deploy the cage. In alternate embodiments, the wire may be made of stainless steel, NITINOL, or plastic (e.g., PEEK). Other possible materials for the repositioning member include other wire materials include tungsten, platinum, iridium platinum, titanium, ELGILOY (Elgin, Ill.), and mixtures thereof, as well as other suitable materials known to those of skill in the art.

Figure 3:
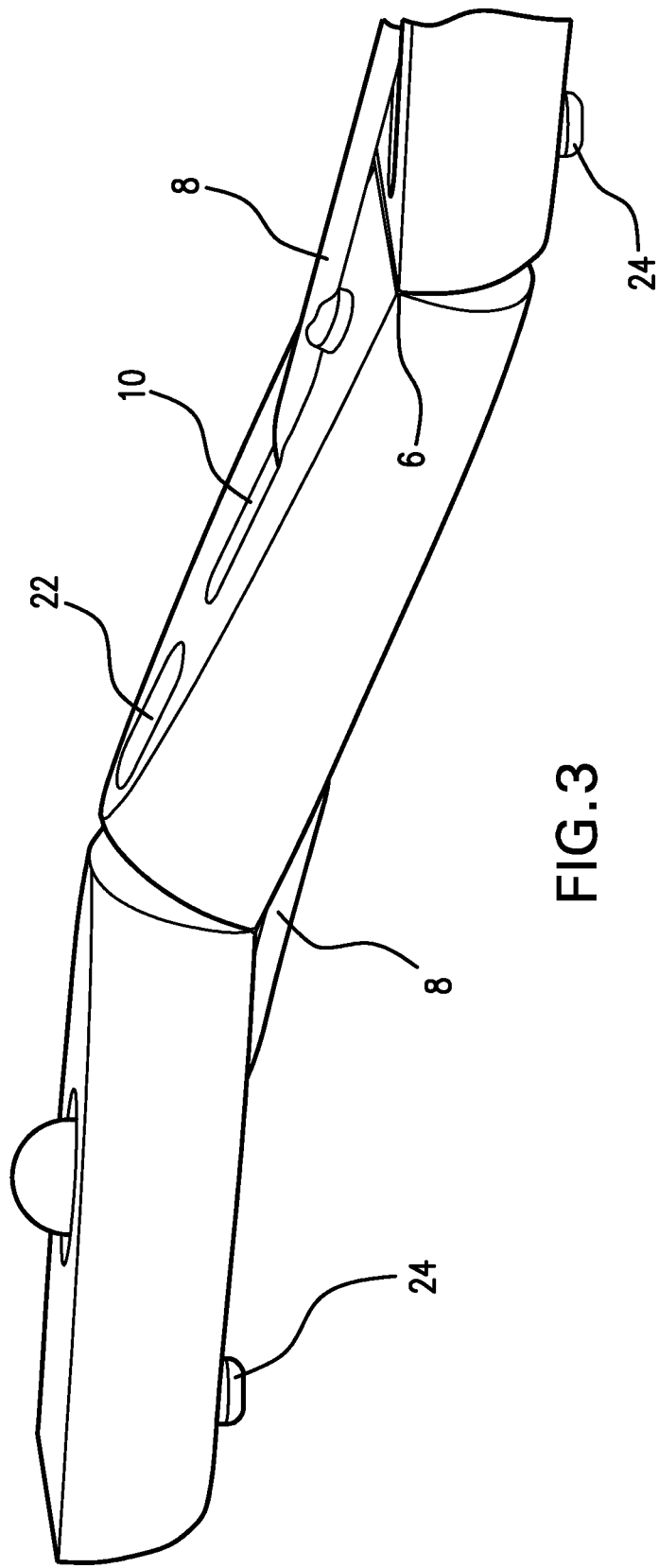
FIG. 3 shows a perspective view of a portion of an expandable device in accordance with one embodiment of the present invention.
Figure 4:
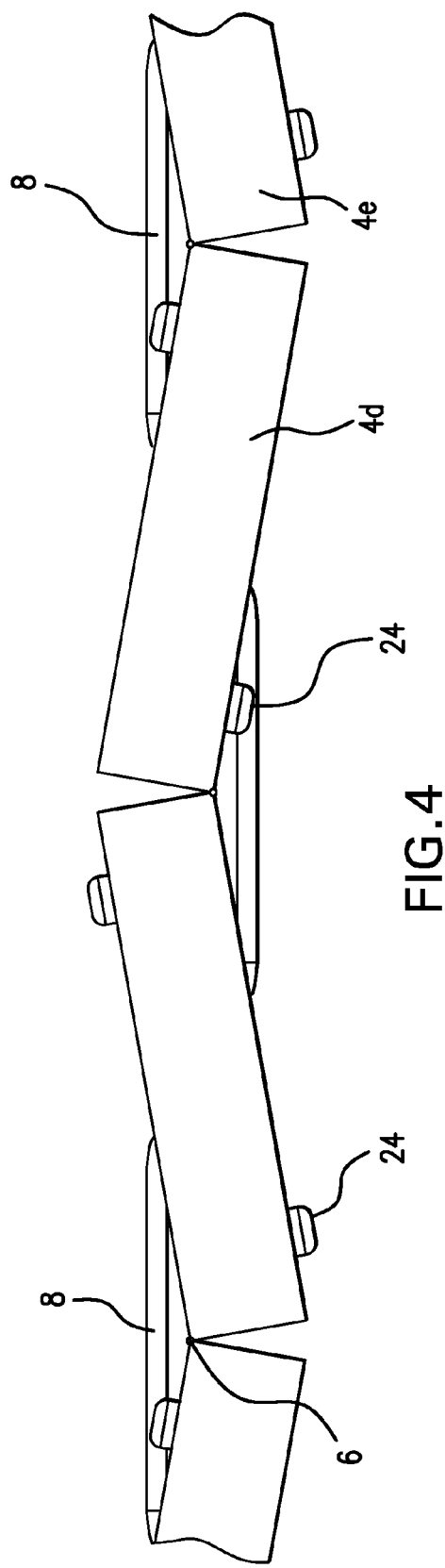
FIG. 4 shows a side view of a portion of an expandable device showing embodiments of a living hinge and repositioning member in accordance with one embodiment of the present invention.
Figure 5:
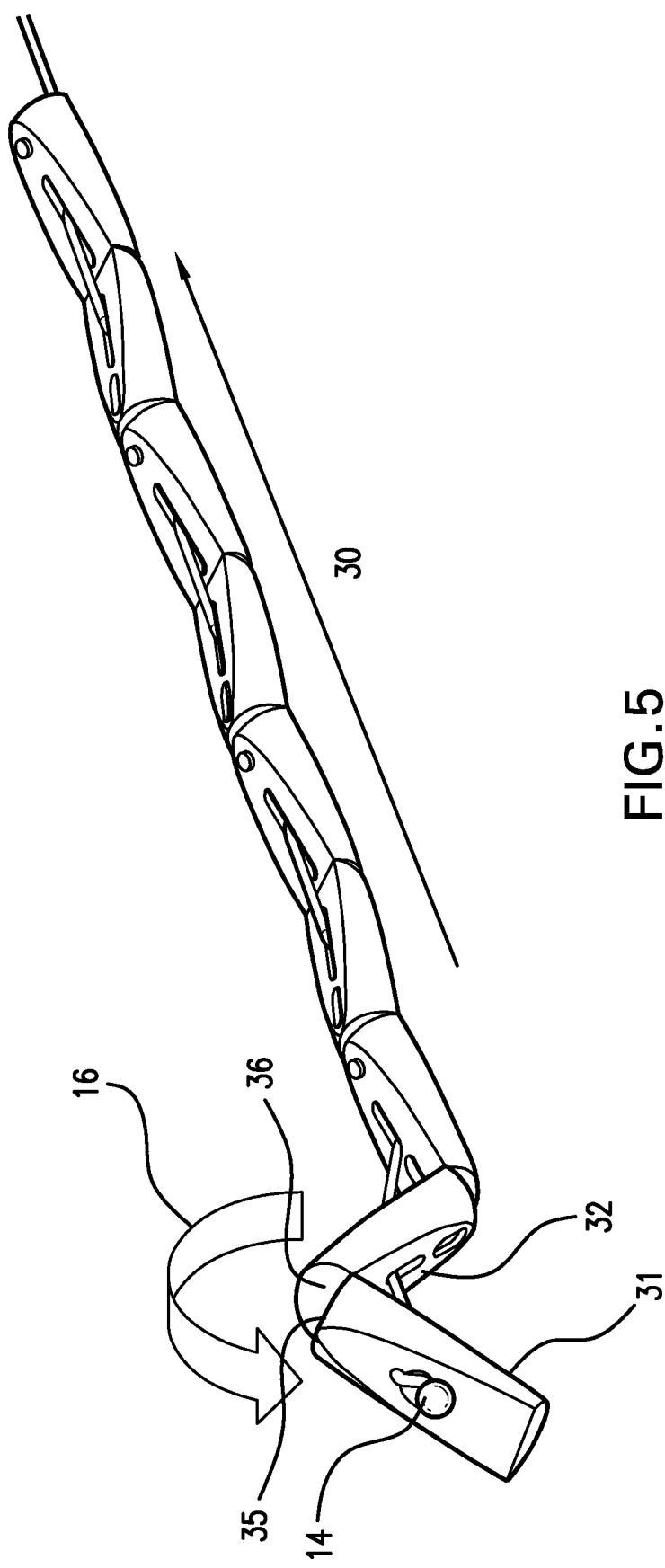
FIG. 5 shows a vertical expansion of a first segment pair of an expandable device in a partially deployed or folded state in accordance with one embodiment of the present invention.

In certain embodiments, the repositioning member may engage each of the segments. The repositioning member 8 may be inserted into an aperture 10 that runs through a portion of the interior of each segment. For example, in one embodiment, the repositioning member is a wire that runs through a central slot 10 in each segment (FIGS. 2-4). As the repositioning member is tightened, for example, by pulling the connector along axis 30 from the distal end of the device 3 to the proximal end of the device 5, adjacent segment pairs will be pulled towards each other 16 such that the axial surfaces 35, 36 become separated, and longitudinal surfaces from at least two adjacent segments, i.e., 31 and 32, become juxtaposed adjacent to each other (FIG. 5). In an embodiment, the repositioning member has an element 14 added to fixedly connect the repositioning member to the distal end such that the repositioning member cannot be pulled through the slots (FIGS. 1, 2 and 4).

Figure 6:
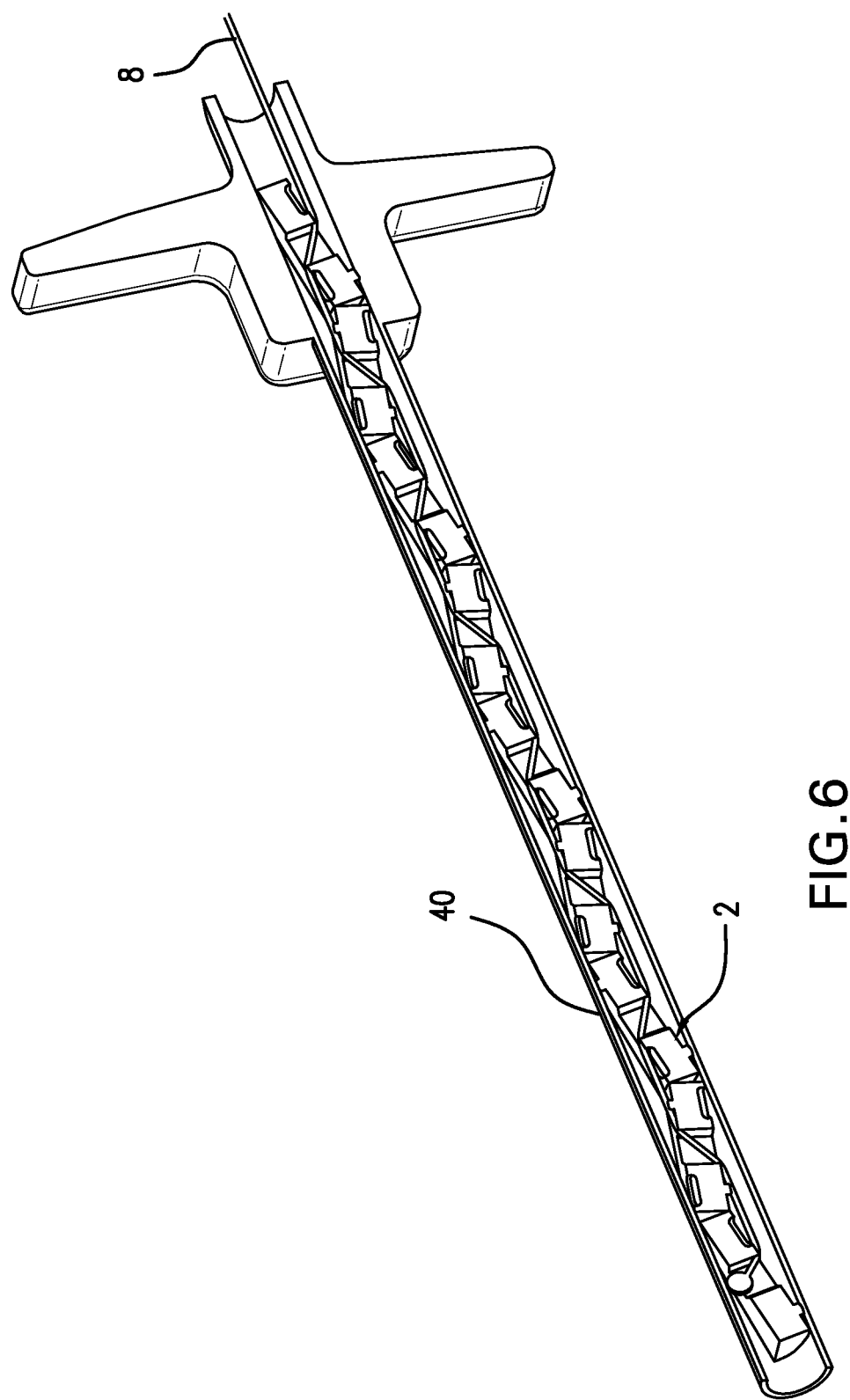
FIG. 6 shows a cross-sectional view of an expandable device being delivered through a cannula in accordance with one embodiment of the present invention.
Figure 7:
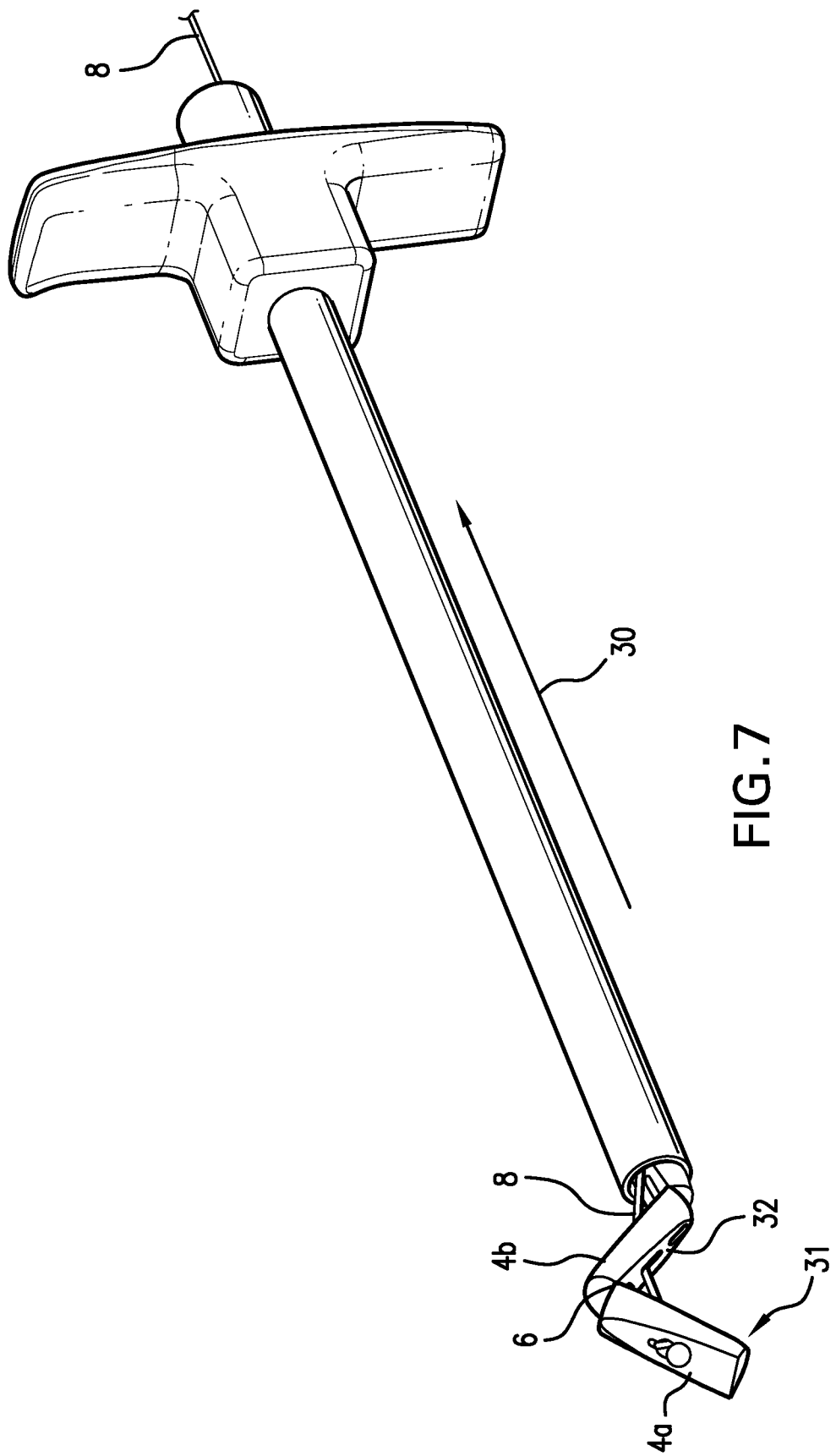
FIG. 7 shows a first segment pair emerging from a cannula and being folded and vertically expanded in accordance with one embodiment of the present invention.
Figure 8:
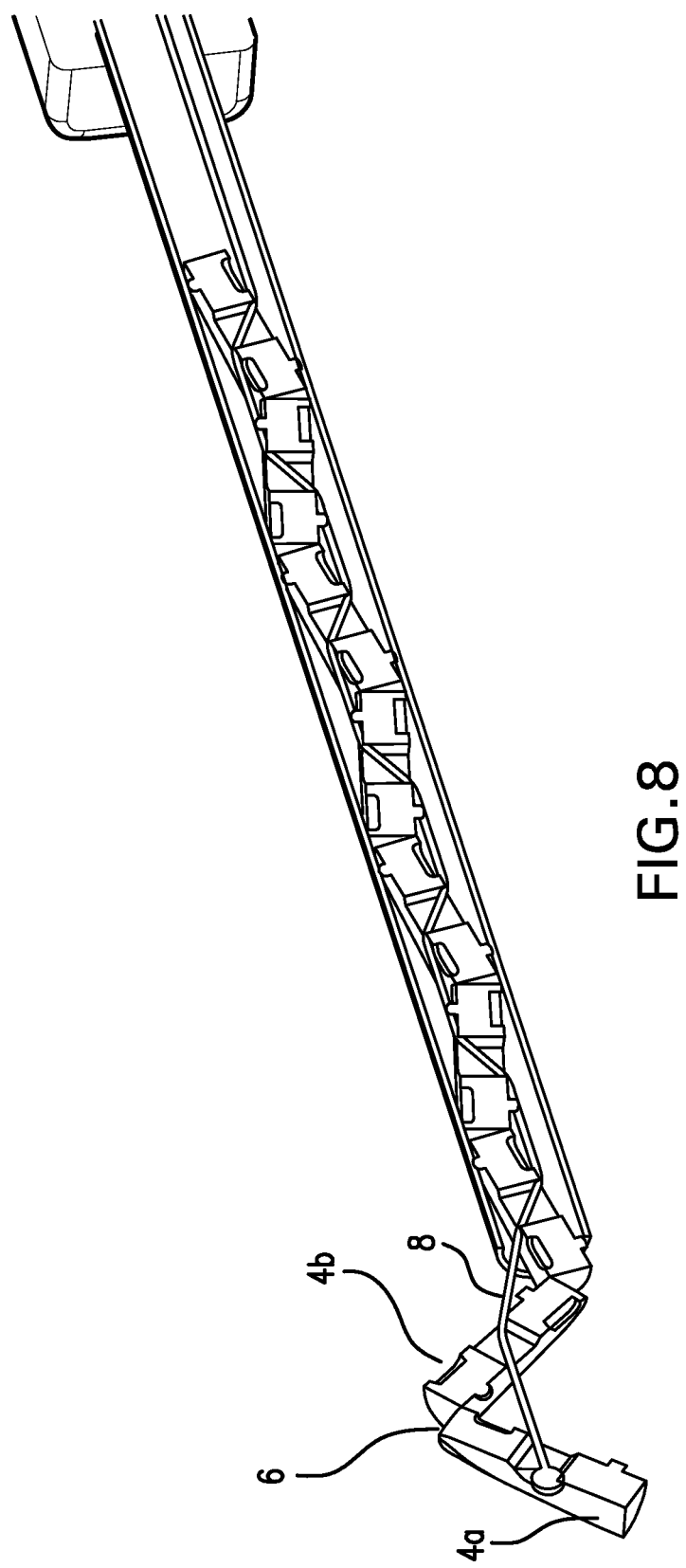
FIG. 8 shows a cross-sectional view of a vertical expansion of a first segment pair emerging from a cannula in accordance with one embodiment of the present invention.

In one embodiment, the undeployed device 2 may be delivered to the intervertebral site requiring repair via an access member such as a cannula 40 (FIG. 6). In such an embodiment, as the repositioning member 8 is tightened by pulling along axis 30, segment pairs 4a, 4b that have emerged from the delivery cannula are forced together, such that the axial surfaces 35, 36 become separated, and one longitudinal surface from each segment, i.e., 31 and 32, become juxtaposed adjacent to each other (FIGS. 6-8). In this way, segment pairs that have emerged from the delivery cannula are forced together, essentially rotating about the living hinge 6 that they share in common.

Figure 9:
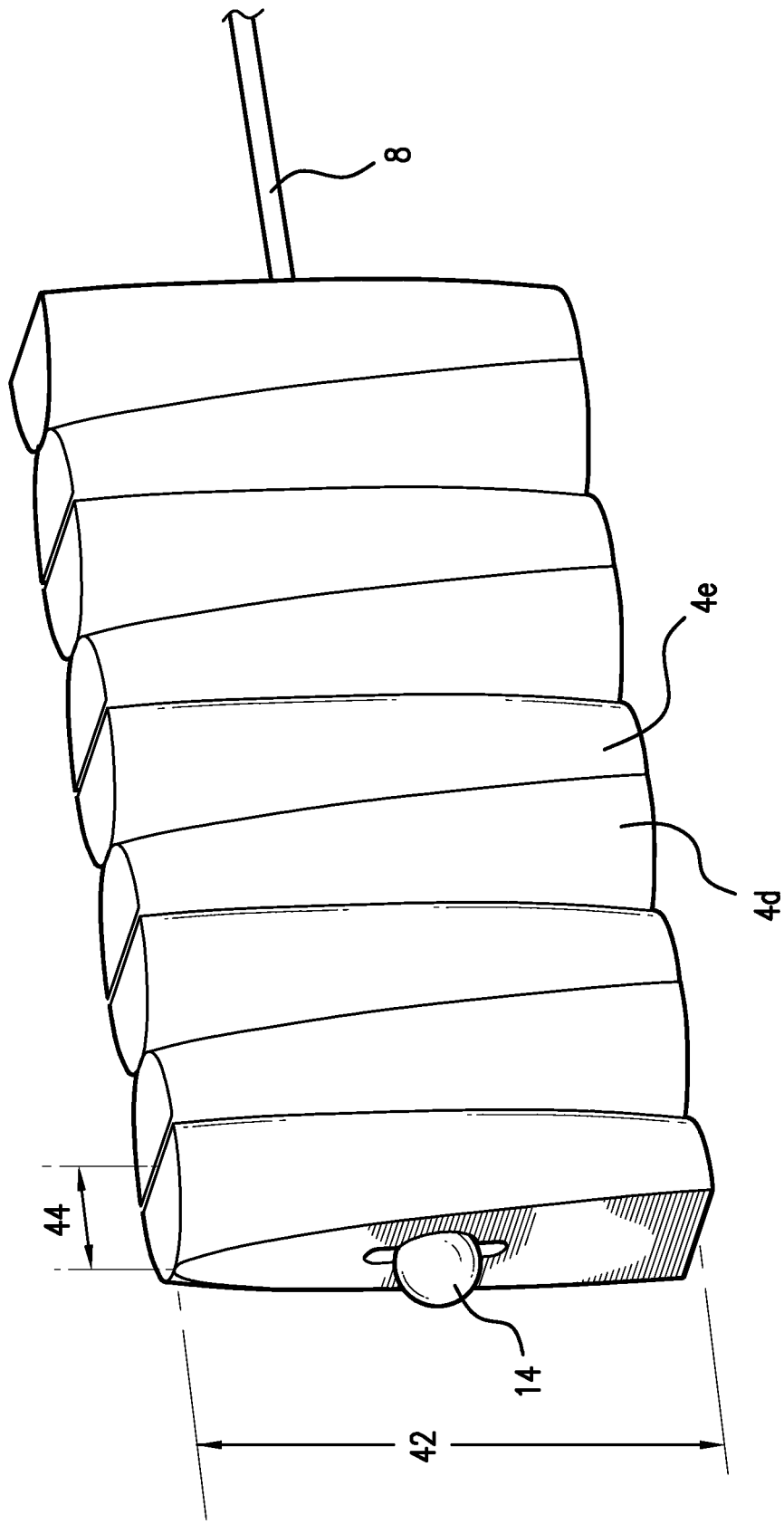
FIG. 9 shows an expandable device in a fully deployed (e.g., folded) state in accordance with one embodiment of the present invention.

It can be seen that the movement can, in certain embodiments, be thought of as a truss structure with a pivot point at its apex, where the living hinge is the apex. As the repositioning member is tightened, the truss-like structure transforms from a fairly flat structure, with a large angle between the segments, to a taller vertical structure in which the angle between the individual segments has narrowed. In certain embodiments, the taller deployed structure has a height 42 that is about 2 to 5 times the height 44 of the undeployed structure (FIG. 9). In the final deployed state, each pair of segments may be vertical such that the angle between them is zero degrees. Or, each pair of segments may have moved from the co-axial plane, but may not be parallel (e.g., FIG. 1B). Once at least two segments have been deployed, another pair of segments sharing a common living hinge may subsequently be pushed out of the delivery cannula, and the repositioning member further tightened, forcing the subsequent pair of segments to expand vertically. The deployment may continue until the entire cage emerges from the cannula (FIGS. 6-8 and 10).

In other embodiments, repositioning member 8 can be an elastic member connected between at least two of segments 4a-4i for pulling the segments towards each other. For example, repositioning member 8 could be fixedly connected to segments 4a (via attachment element 14) and 4i (via an attachment element substantially similar to attachment element 14). Note that in such a construction, member 8 would not need to extend beyond segment 4i as depicted in FIG. 2. By providing a force drawing segments 4a and 4i together, elastic member 8 would bias device 2 towards its expanded (i.e., substantially folded) configuration.

Emplacement of such a device into a body part could then involve stretching member 8 to place device 2 in its substantially unfolded configuration, and restraining device 2 in that configuration by placing device 2 within a cannula. The distal end of the cannula could then be positioned at the target body part (e.g., via percutaneous access), and device 2 could then be pushed from the cannula at that location. Because of the force of elastic member 8 pulling segments 4a-4i together, device 2 automatically folds up into its expanded configuration as it exits the cannula.

Figure 11:
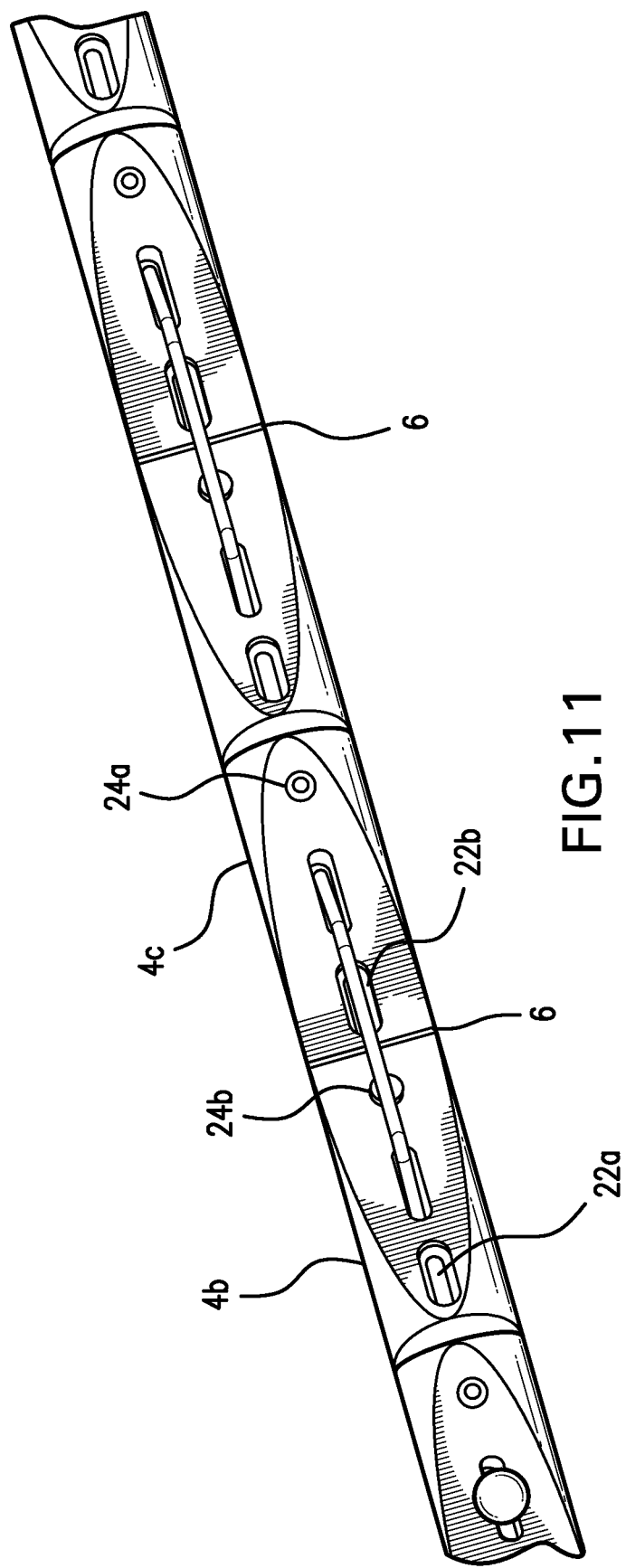
FIG. 11 shows a top view of an expandable device in an undeployed (e.g., unfolded) state in accordance with one embodiment of the present invention.
Figure 12:
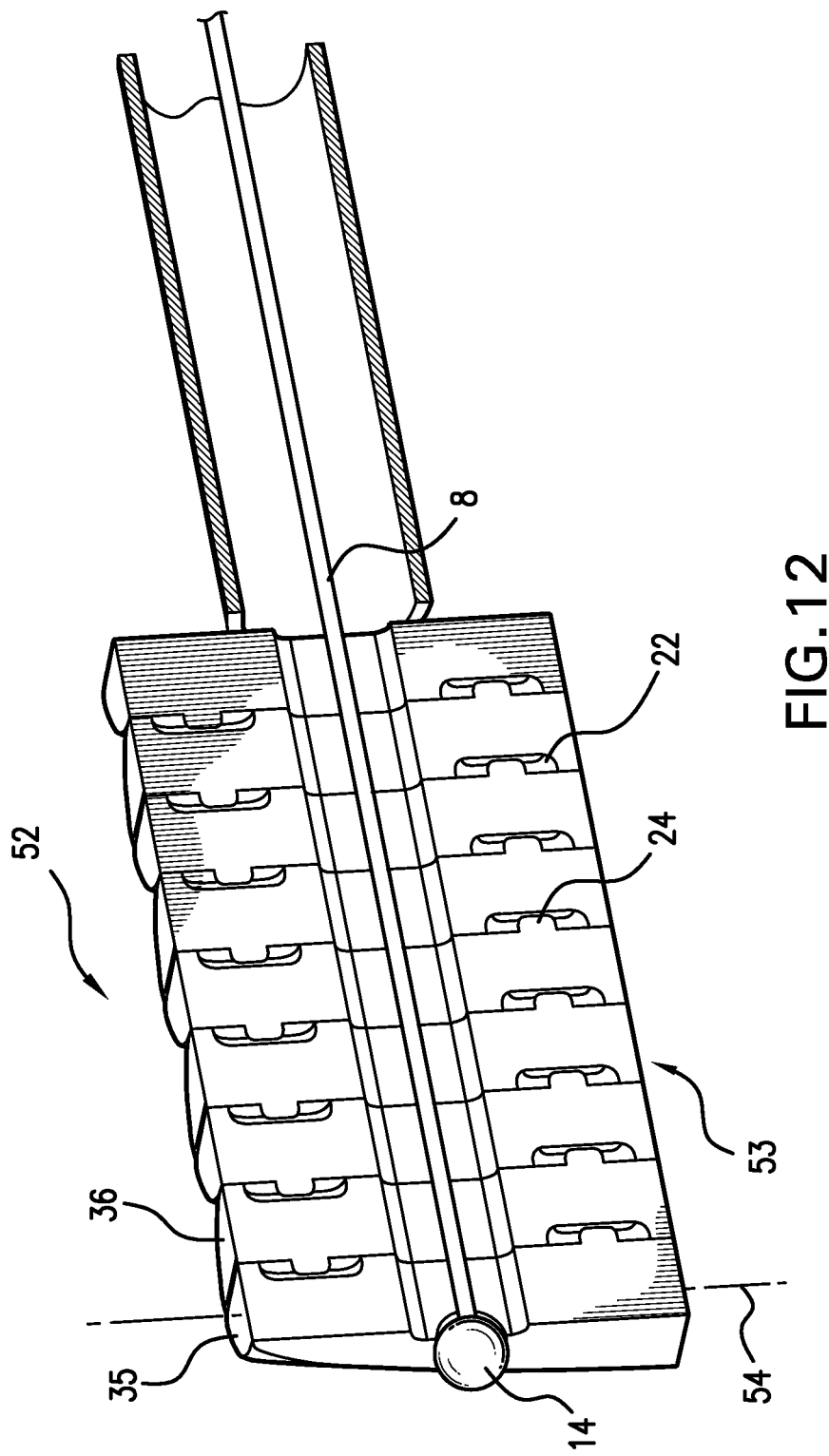
FIG. 12 shows a cross-sectional view of an expandable device in a fully deployed (e.g., folded) state and having emerged from a cannula in accordance with one embodiment of the present invention.

In certain embodiments, the segments are interlocked in a manner to prevent lateral shifting between the each pair of deployed segments. For example, the segments may comprise a protrusion or protrusions that fit into an aperture or apertures on neighboring segments. I some embodiments, the protrusions may be pins and the apertures may be slots. In some cases, the protrusions may be positioned near the end of a segment so as to fit into an aperture at the end of an adjacent segment. Alternatively or additionally, a plurality of protrusions may be fashioned on each segment to fit into a plurality of apertures in an adjacent segment. For example, as shown in FIG. 11, as the device is deployed, pin 24a on the proximal end of segment 4c may fit into slot 22a positioned on the distal end of segment 4b. Also, pin 24b positioned on the proximal end of segment 4b may fit into slot 22b positioned on the distal end of segment 4c. As the expandable device is deployed, the pins will fit into the slots on adjacent segments, thereby preventing, or reducing, any lateral shifting between the cages along both vertical axis 54 and the corresponding horizontal axis (FIG. 12). In this way, the upper and lower surfaces 52, 53 that are presented to the body part into which the device is inserted are substantially flat. Although the embodiment shown utilizes pins and slots, it will be understood that any type of male/female connector system may be employed.

Figure 10:
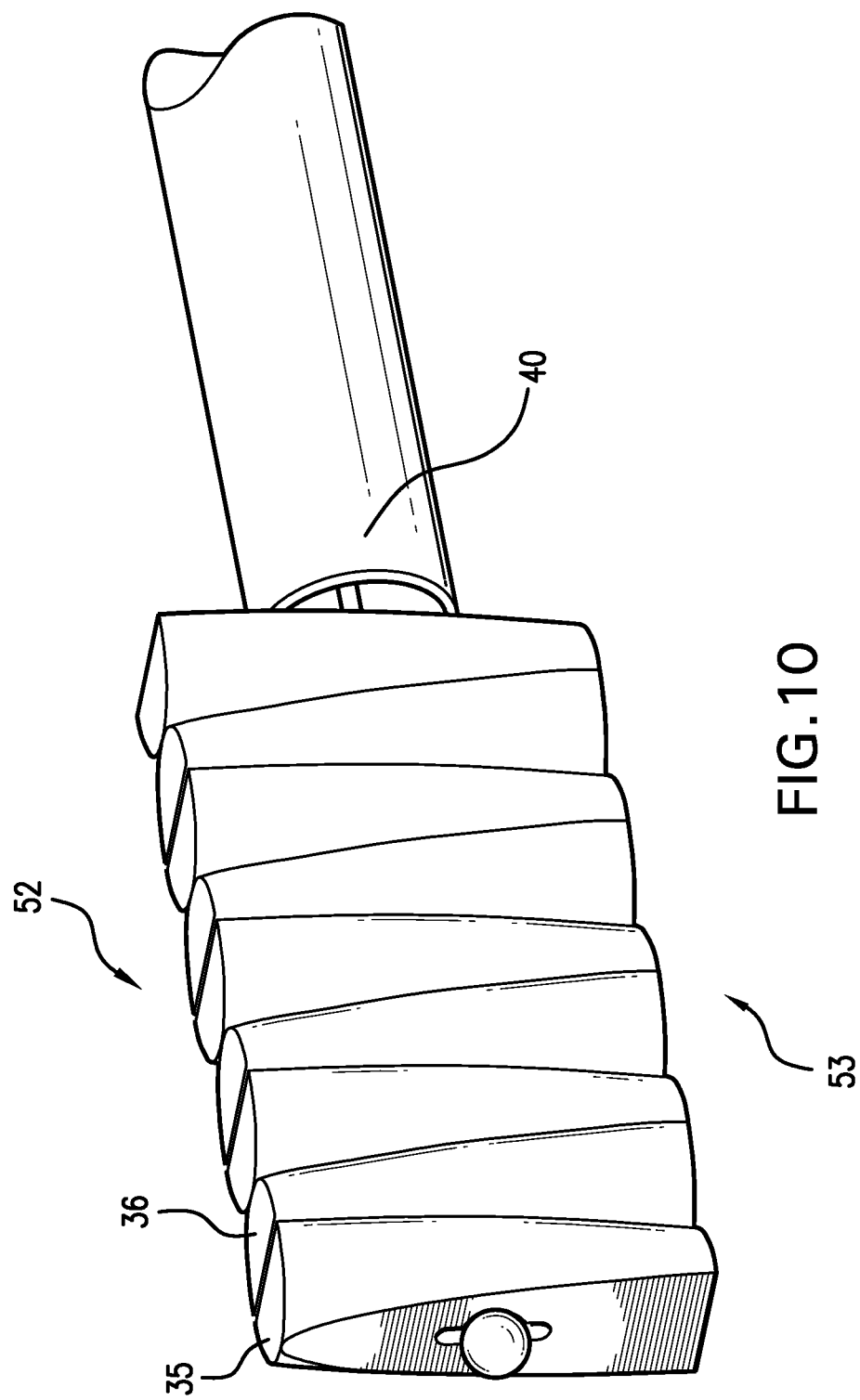
FIG. 10 shows an expandable device in a fully deployed (e.g., folded) state and having emerged from a cannula in accordance with one embodiment of the present invention.
Figure 13:
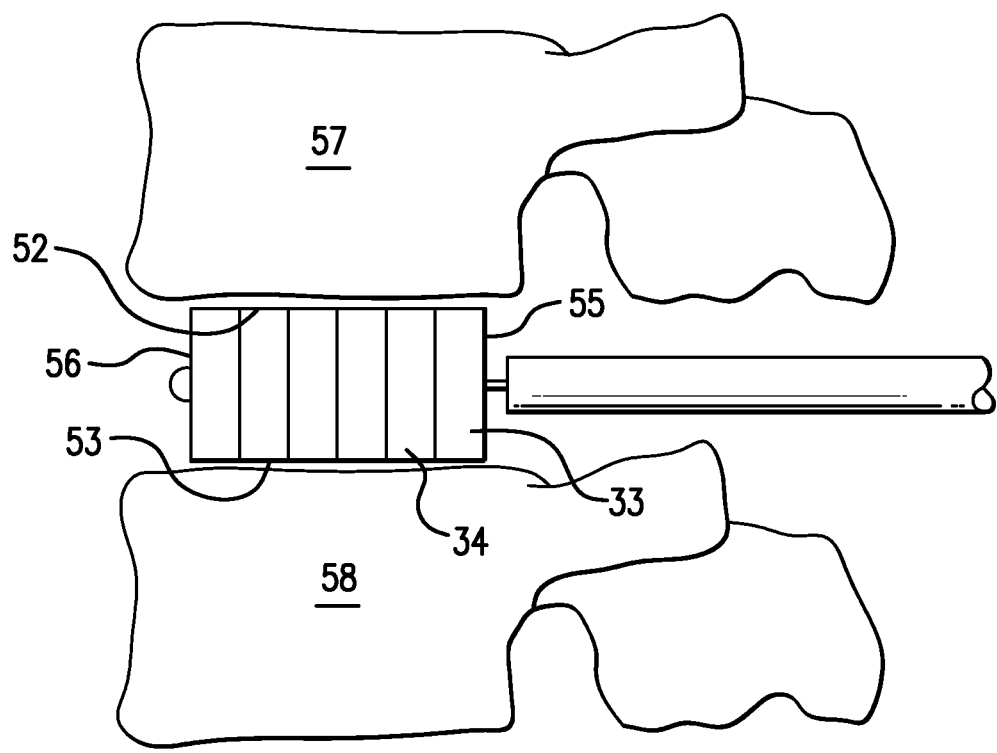
FIG. 13 shows a side view of an expandable device deployed between two vertebral bodies in accordance with one embodiment of the present invention.

The segments that make up the expandable device may be fashioned from a variety of shapes that are designed to interlock. In one embodiment, the segments are a shape such that the area of each of the upper and lower surfaces 52, 53 of the deployed expandable device is maximized so as to increase contact between the expandable device and the body part into which the device is inserted (FIG. 10). Also, the shape of the segments may be chosen such that each of the upper and lower surfaces 52, 53 are substantially flat. In this way, a flat surface is presented to the body parts that are in contact with the expandable device once it has been deployed and emplaced in situ. For example, as shown in FIG. 13, when the expandable device is deployed between to vertebral bodies, the upper surface 52 may contact the upper vertebral body 57, and the lower surface 53 may contact the lower vertebral body 58. Or, the expandable device may be designed such that the upper and lower surfaces are slightly angled by using segments having different sizes. For example, the expandable device may be designed such that the segments on one end of the expandable device are slightly shorter than the segments on the other end of the expandable device (FIG. 1F). In this way, the expandable device may be taller at one end e.g., the proximal end, 55, than the other end, e.g., the distal end 56 (FIG. 13). It is to be understood that as used herein, upper and lower are used interchangeably. In most embodiments, the expandable device is symmetrical and so may be rotated 180 degrees such that the top surface may be used as the bottom surface.

Or, the segments may be designed such that the axial surfaces have a somewhat roughened texture. For example, the surfaces may be stippled or slightly ribbed such that when the device is deployed, the upper and lower surfaces 52, 53 will be able to engage the body part into which the expandable device has been emplaced. The stippled or ribbed edges may facilitate the addition of bone grafts or other materials that may be used in conjunction with the expandable device. In an alternate embodiment, the upper and lower surfaces 52, 53 may have protrusions, as for example where the segments have axial surfaces that are not perpendicular to the longitudinal surfaces (see e.g., FIGS. 1C and 1D) so as to allow the protrusions to engage the body part into which the expandable device has been emplaced.

In an embodiment, the expandable device, when it is in its non-deployed or substantially unfolded state, is of a size that allows the expandable device to be delivered to the desired position between two vertebrae through a cannula. In a variation of this embodiment, the expandable device can not pass through the same cannula when it is in its deployed or substantially folded (i.e., expanded) state. In this variation, the expandable device will be delivered to the desired site between two adjacent vertebrae in its unexpanded state and then expanded to its expanded state.

In one embodiment, each of the segments may be shaped as a portion of a cylinder, with opposing flat surfaces 31, 32 along the top and the bottom of the expandable device, and rounded or arcuate surfaces as the side walls, 33, 34 (FIG. 2). Also, shown in FIG. 2 are axial ends 35, 36. In this way, the segments can have the adjacent surfaces 31, 32 (FIG. 2) be substantially flush with each other when the expandable device is deployed, whereas the side walls are shaped to be compatible with the inner surface of a cylindrical cannula. In other embodiments, the segments can be any of a plurality of shapes. Thus, other polygonal, cylindrical, or oval-like shapes are contemplated, such as segments that are cylindrical, rectangular, trapezoidal, rhomboid, oval or the like. Any shape can be used as long as there exists a surface that allows the segments to fold to the extent required.

In certain embodiments, it is desired that the expandable device of the present invention can be incorporated by minimally invasive surgery. In such embodiments, the expandable device in its undeployed state should be able to fit through an access member. In certain embodiments, the access member may comprise a cannula. In one embodiment, the cannula may be on the order of a 6 mm inner diameter. In certain embodiments, flat longitudinal faces may provide good surfaces for interlocking of the segments. In one embodiment, the living hinges are designed to have sufficient strength so that the expandable device can attain its expanded state and still perform its intended function.

In one embodiment, the expandable device is configured to have a substantially rectangular shape when the cage is deployed. In this embodiment, the side walls 33, 34 may be arcuate such that the expandable device, when in its undeployed state, has an outer surface that generally cylindrical. In this way, the expandable device can be deployed via a cylindrical access member, such as a cylindrical cannula. It should be understood that in the embodiment where the expandable device is used to replace an intervertebral disc for a spinal fusion, the shape of the expandable device can be any shape that will provide the needed positioning and stabilizing of the vertebrae during the fusion procedure and after the administration of the agent used to promote fusion. For example, the expandable device should be able to provide support and structure for degenerative disc diseases, Grade I or II spondylolistheses, adult scoliosis and other disorders of the lumbar spine as well as for any other purpose.

The size of the expandable device may be varied depending upon the body part into which the expandable device will be emplaced. For example, for fusion of adjacent vertebral bodies, in alternate embodiments the segments that comprise the expandable device range from between about 0.2 to 2.0, or 0.3 to 1.0 cm in height, 0.2 to 2.0 or 0.3 to 1.0 cm in width, and 0.2 to 5.0, or 0.3-3.0 cm in length. In a variation, the height can be from about 3 to 6 mm, the width from about 3 to 6 mm, and the length from 3 to 20 mm. It should be recognized that although in the above description height and length have been differentiated, it should be recognized that the height can also be length of the various segments (that is, after deployment/expansion of the expandable device the length become the height of the cage). Alternatively, the dimensions of the expandable device may be determined by referencing the available range of heights for expandable devices/vertebral body replacements currently on market. The dimensions may be varied such that the deployed device has dimensions suitable for placement between the vertebrae of a normal sized adult patient. However, it should be understood that other sizes are contemplated and therefore within the scope of the invention, for example, when the expandable devices are used on children or on adults that are of smaller or larger stature.

The expandable device may comprise any number of segments depending upon the body part into which the expandable device is to be inserted. Also, the segments may vary with respect to the relative ratio between the diameter (or width and/or height of the segment) as compared to the length. In alternate embodiments, the length of each segment is about 1.5 to 10, or 1.2 to 5, or 2 to 3 times the diameter (or width and/or height) of the segment.

In an embodiment, the expandable device is made of materials that are appropriate for being inserted in between vertebrae. For example, the segments may be made of PEEK (-polyetheretherketones), titanium, stainless steel, ultra high molecular weight polyethylene, nylon or polycarbonate. The hinge(s) and/or repositioning member(s) may be made of the same material as are the segments, or may be made of different materials as the segments and/or may be made of different materials than each other. In alternate embodiments, the hinges and/or repositioning members may be made of titanium, stainless steel or NITINOL (i.e., a nickel titanium alloy). It should be understood that for either the segments, hinges or the repositioning member, other materials are contemplated such as silicone and metal materials, tantalum, platinum, titanium, and niobium alloys, PHYNOX®, or any of a plurality of polymeric materials, such as polytetrafluoroethylene (ePTFE).

Other materials/chemicals may be associated with the expandable device of the present invention such as lubricants, antibiotics, anti-cancer agents, bone cements, bone grafts, chemicals that prevent autoimmune defenses, and the like. In an embodiment, these materials/chemicals may be released over an extended time period. These materials/chemicals may be used to aid accretion of bone or of tissue, to aid in fighting off bacterial infections, to promote tissue growth or for a plurality of other reasons.

Methods of Emplacing an Expandable device in a Body Part

In certain embodiments, the present invention comprises methods for emplacing an expandable device in a body part. For example, in one embodiment, the present invention comprises a method of emplacing an expandable device comprising a plurality of connected segments in a body part in a subject comprising: (a) emplacing the expandable device in a cannula in a first configuration, wherein a plurality of longitudinal axes of the plurality of connected segments are substantially unfolded; (b) urging the distal end of the cannula to the body part of interest; (c) urging the expandable device through the cannula into the body part of interest; and (d) causing the plurality of connected segments to assume a second configuration in the body part of interest wherein the plurality of connected segments are substantially folded to expand the expandable device to an expanded height, and wherein at least one of the plurality of connected segments substantially spans the expanded height.

In some embodiments, the plurality of longitudinal axes of the plurality of connected segments are substantially co-axial in the first configuration. The plurality of segments may be folded in alternating directions in the second configuration. Also in some embodiments, the plurality of longitudinal axes of the plurality of connected segments are substantially parallel. For example in certain embodiments, a longitudinal surface of a first one of the plurality of connected segments is substantially flush with a longitudinal surface of a second one of the plurality of connected segments in the second configuration. Thus, in one embodiment, the plurality of connected segments have a first configuration wherein a plurality of longitudinal axes of the plurality of connected segments are substantially coplanar, and a second configuration wherein the plurality of connected segments are folded in alternating directions. In one embodiment, the expandable device comprises a first member comprising a plurality of segments that may fold in a coordinated manner from a first configuration in which the segments are linearly aligned such that an axial end of each segment is substantially flush with an axial end of an adjacent segment, to a second configuration wherein a longitudinal surface of at least one segment is substantially flush with a longitudinal surface of a second, adjacent segment.

In an embodiment, the device expands (i.e., folds) as it exits the cannula. Thus, the method may comprise emplacing the device in a cannula; (b) urging the distal end of the cannula to the body part of interest; (c) urging at least a portion of the device to exit the cannula such that at least two of the segments exit from the distal end of the cannula into the body part of interest; (d) causing the portion of the device that has exited the cannula to assume the second configuration (either automatically as the device exits the cannula or via manual actuation); (e) repeating steps (c) and (d) until the expandable device has completely exited the cannula and has been fully deployed.

The segments used in the expandable device of the method of the present invention may be separate parts, or the segments may be joined together as a single unit. For example, in one embodiment, the segments are connected to each other by a hinge between adjacent segments. In certain embodiments, the plurality of connected segments are connected by a plurality of hinges, each of the plurality of hinges having a thickness less than a thickness of each of the plurality of connected segments. For example, in some embodiments, the plurality of connected segments are connected by living hinges.

In one embodiment, the device comprises a repositioning member for urging the first member between the first configuration and the second configuration. For example, the repositioning member may engage each of the segments, such that the repositioning member can be used to urge the expandable device from a first configuration in which the segments are substantially unfolded to a second configuration in which the segments are substantially folded. In one embodiment, the first configuration comprises having an axial end of each segment being substantially flush with an axial end of an adjacent segment, and the second configuration comprises having a longitudinal surface of at least one segment being substantially flush with a longitudinal surface of a second segment. In one embodiment, the repositioning member is a wire. The wire may, in certain embodiments, be fixedly attached to the distal-most segment. For example, in one embodiment, step (d) may comprise tightening the repositioning member by pulling the repositioning member from the distal end of the device towards the proximal end of the device such that the two segments that have emerged from the cannula become substantially folded.

In some embodiments, the repositioning member may comprise a wire that is passed through at least one aperture on each of the segments. The wire may pass through the segments in an alternating manner. For example, the wire may loop through an aperture positioned in each of the segments in a manner so as to extend from a first segment to a second segment on one face of the unit (e.g., upper or superior) and then to extend from the second segment to the third segment on the opposite face of the unit (e.g., lower or inferior). The wire may then extend from the third segment to the fourth segment on the superior face, and from the fourth segment to the fifth segment on the inferior face, and so forth, until all of the segments are connected.

The positioning of the wire relative to the upper and lower faces of the unit can allow for the wire to function so as to collapse the upper and lower faces (i.e., longitudinal surfaces) of the segments together such that the longitudinal surfaces of adjacent segments go from a substantially linear arrangement, to an arrangement where the longitudinal surfaces of adjacent segments are pulled together. In certain embodiments, the step of causing the plurality of connected segments to assume the second configuration comprises moving a distal one of the plurality of connected segments and a proximal one of the plurality of connected segments closer together. Thus, in one embodiment, the wire is fixedly attached to a segment positioned on one end of the device such that the when the wire is pulled toward the other segments, the adjacent segments are pulled towards each other such that the longitudinal surface of one segment is urged to a final configuration in which it is substantially flush with the longitudinal surface of a second segment. In one embodiment, the wire may be pulled such that it is completely tightened (i.e., can be pulled no further). At this point, the device will have a configuration such that at least one longitudinal surface of each segment is substantially flush with at least one longitudinal surface of an adjacent segment.

The expandable device, when fully deployed, may have a height that is equal to the longitudinal length of each segment. In certain embodiments, the segments may comprise elements to assist in the alignment of the segments when the longitudinal surfaces of at least two segments are substantially flush. In this way, the tendency of the segments to twist off center and become misaligned can be reduced. For example, in one embodiment, the alignment elements may comprise at least one protrusion on a first segment and at least one aperture to receive the protrusion on an adjacent segment. Or, multiple protrusions and apertures may be used. Generally, each of the segments may comprise at least two protrusions and receiving apertures. For example, in one embodiment, the protrusions and receiving apertures are positioned close to the axial end of each segment. In this way, when each pin and aperture interlock, the mating will prevent the two segments from twisting or wiggling relative to the longitudinal (i.e., longest) axis of the longitudinal surface.

The method may employ additional tools to stabilize the body part of interest during the procedure. For example, in one embodiment, the method may comprise emplacing an inflatable member into the body part to support the body part during emplacement of the expandable device. In certain embodiments, the inflatable member may remain in place until the procedure is completed. Also, in some embodiments, a plurality of inflatable members may be used. For example, a first and second inflatable member may be positioned in the body part prior to insertion of the cannula containing the expandable device. After expansion of the cage, and any other therapeutic steps, the inflatable members may be removed.

Expandable devices of the present invention may be designed for emplacement in a variety of body parts. For example, the expandable devices may be emplaced in a boney structure, or between two bones. In one embodiment, the segments are configured for percutaneous delivery to a body part using a cannula. For example, the step of causing the plurality of connected segments to assume a second configuration may comprise causing the plurality of connected segments to exit the cannula.

In certain embodiments, the body part may comprise a spinal disc or an intervertebral region between two vertebral bodies. In one embodiment, the expandable device may be emplaced between two vertebral bodies, to replace the intervertebral disc. The methods of the present invention allow the treatment of any vertebrae, for example, the expandable device can be applied to pelvic, lumbar, thoracic, or cervical vertebrae. Where the expandable device is emplaced between two vertebral bodies, the access may be extrapedicular or transpedicular. Or, an anterior access may be used. For example, where the expandable device is emplaced between two vertebral bodies as part of a bone graft procedure, the method may comprise emplacing a bone graft material to promote fusion of a vertebral body that is adjacent to the upper surface of the disc to a vertebral body that is adjacent to a lower surface of the disc after the device has been emplaced. Thus, embodiments of the present invention may be used as expandable devices for insertion between two vertebral bodies during a spinal fusion procedure. Or, the expandable device may be used for emplacement in other body parts such as within a vertebral body or other bone structure.

In certain embodiments, the expandable device is fashioned for percutaneous access. For example, the expandable device may be fashioned for repair of a spine. For example, the method may comprise the step of emplacing the expandable device in a cannula, wherein the expandable device comprises a first member comprising a plurality of segments connected by living hinges, and a wire as the repositioning member that engages each of the segments, wherein the wire can be loosened to allow the segments to be positioned such that the segments are substantially unfolded (e.g., the axial end of one segment is substantially flush with an axial end of an adjacent segment), or the wire can be tightened such that the segments are substantially folded (e.g., the longitudinal surface of one segment is substantially flush with the longitudinal surface of a second segment). The method may also comprise urging the distal end of the cannula to the intervertebral disc region between the two vertebral bodies to position the expandable device to the position where it is to be deployed. The method may also comprise urging a portion of the expandable device to exit the cannula such that at least two of the segments exit from the distal end of the cannula into the intervertebral disc region. The method may further include tightening the wire by pulling the wire towards the proximal end of the cannula such that the two segments that have emerged from the cannula become deployed so as to be substantially folded. Next, the method may include repeating the deployment of adjacent segments until the expandable device has completely exited the cannula and has been fully deployed in the intervertebral region. At this point, the method may comprise adding a bone graft material to the intervertebral region and/or removing the cannula from the intervertebral disc space. Thus, the present invention may, in certain embodiments, comprise a method of emplacing an expandable fusion cage comprising a plurality of connected segments in an intervertebral region between two vertebral bodies in a subject comprising: (a) emplacing the expandable fusion cage in a cannula in a first configuration wherein a plurality of longitudinal axes of the plurality of connected segments are substantially coaxial; (b) urging the distal end of the cannula to the intervertebral region; (c) urging the plurality of connected segments through the cannula into the intervertebral region; (d) moving a proximal one of the plurality of connected segments and a distal one of the plurality of connected segments closer together over a repositioning member threaded through the plurality of connected segments to place the plurality of connected segments in a second configuration by pulling the repositioning member such that the at least two segments that have emerged from the cannula become deployed such that a longitudinal surface of one segment is substantially flush with a longitudinal surface of an adjacent segment; (e) repeating steps (c) and (d) until the expandable fusion cage has completely exited the cannula and has been fully deployed in the intervertebral region; (f) optionally, adding a bone graft material; and (g) removing the cannula from the intervertebral disc space.

As described herein, where the expandable device is used for spinal fusion, the access path may comprise a percutaneous access to the spine. For example, the access member may be a cannula or catheter configured for accessing the spine. In certain embodiments, the access member is configured for accessing the vertebral body. Or, the access member may be configured for accessing the intervertebral disc space. In this embodiment, the entry point may be posterolateral, through Kambin's triangle, or by a typical discography approach. Where the body part is a vertebral body or an intervertebral disc space, two entry points may be used as in a bilateral approach.

The expandable device may also be emplaced in a void that is either within or between two body parts. For example, where the expandable device is being emplaced between two vertebral bodies, as for example to replace a degenerated intervertebral disc and fuse the two vertebral bodies together (spinal fusion), the expandable device may be emplaced in a void that has been generated between the two vertebral bodies.

In one embodiment, the expandable device may be inserted into the body part of interest and expanded without the use of extraneous tools or support structures. Alternatively, a temporary support structure may be used to hold the body part or body parts of interest in position and/or to stabilize the void into which the expandable device is to be emplaced. For example, in some cases, a balloon or balloons may be used to stabilize two vertebral bodies in position while the expandable device is emplaced between the vertebral bodies during a spinal fusion procedure.

Figure 14:
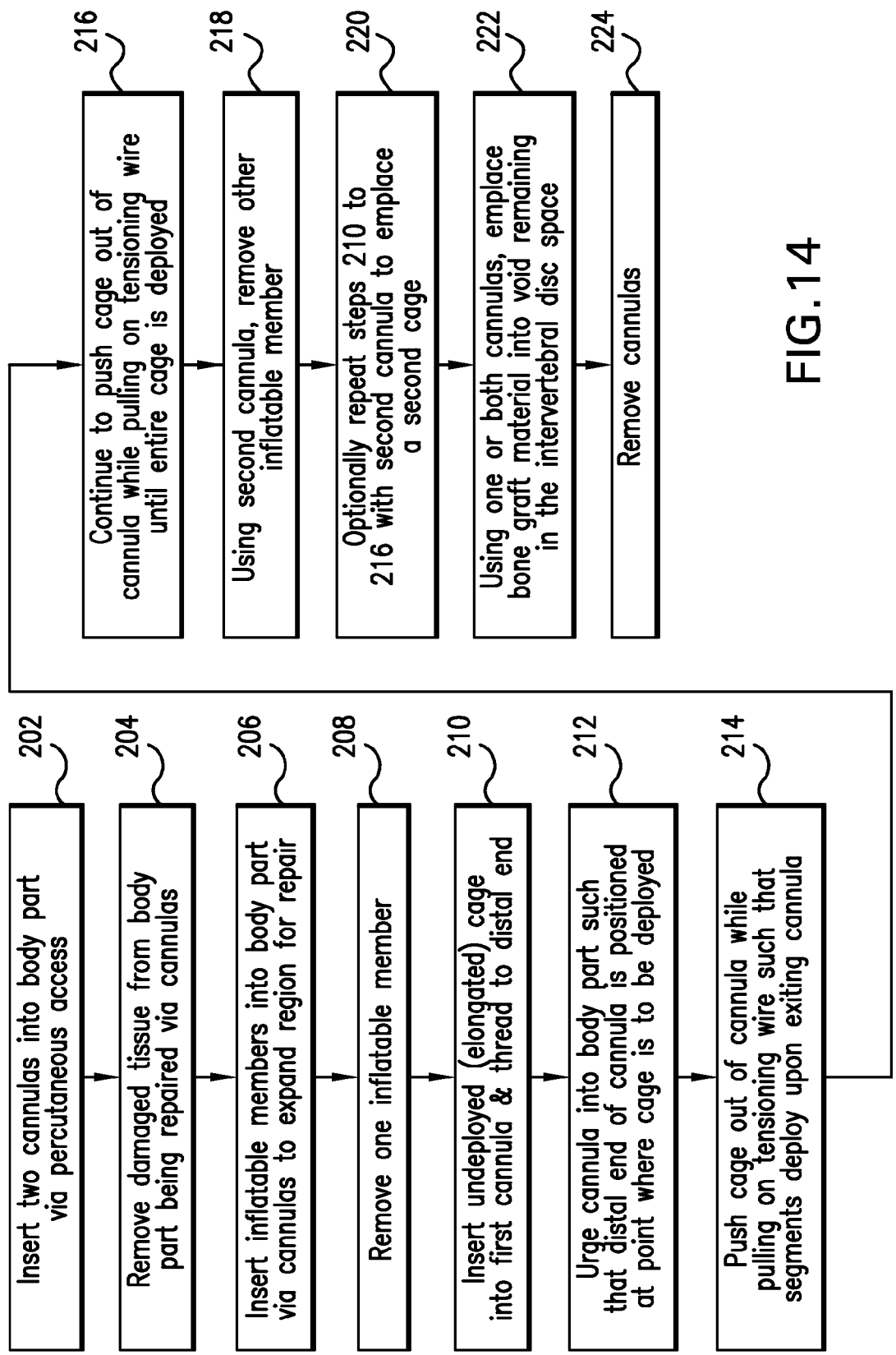
FIG. 14 is a flowchart illustrating a method of using an expandable device comprising a fusion cage in accordance with one embodiment of the present invention.

FIG. 14 shows a flowchart for an example of a method for deploying an expandable device of the present invention. FIGS. 14-22 illustrate an embodiment of an expandable device of the invention being used as a expandable device for fusing two adjacent vertebral bodies.

Figure 15:
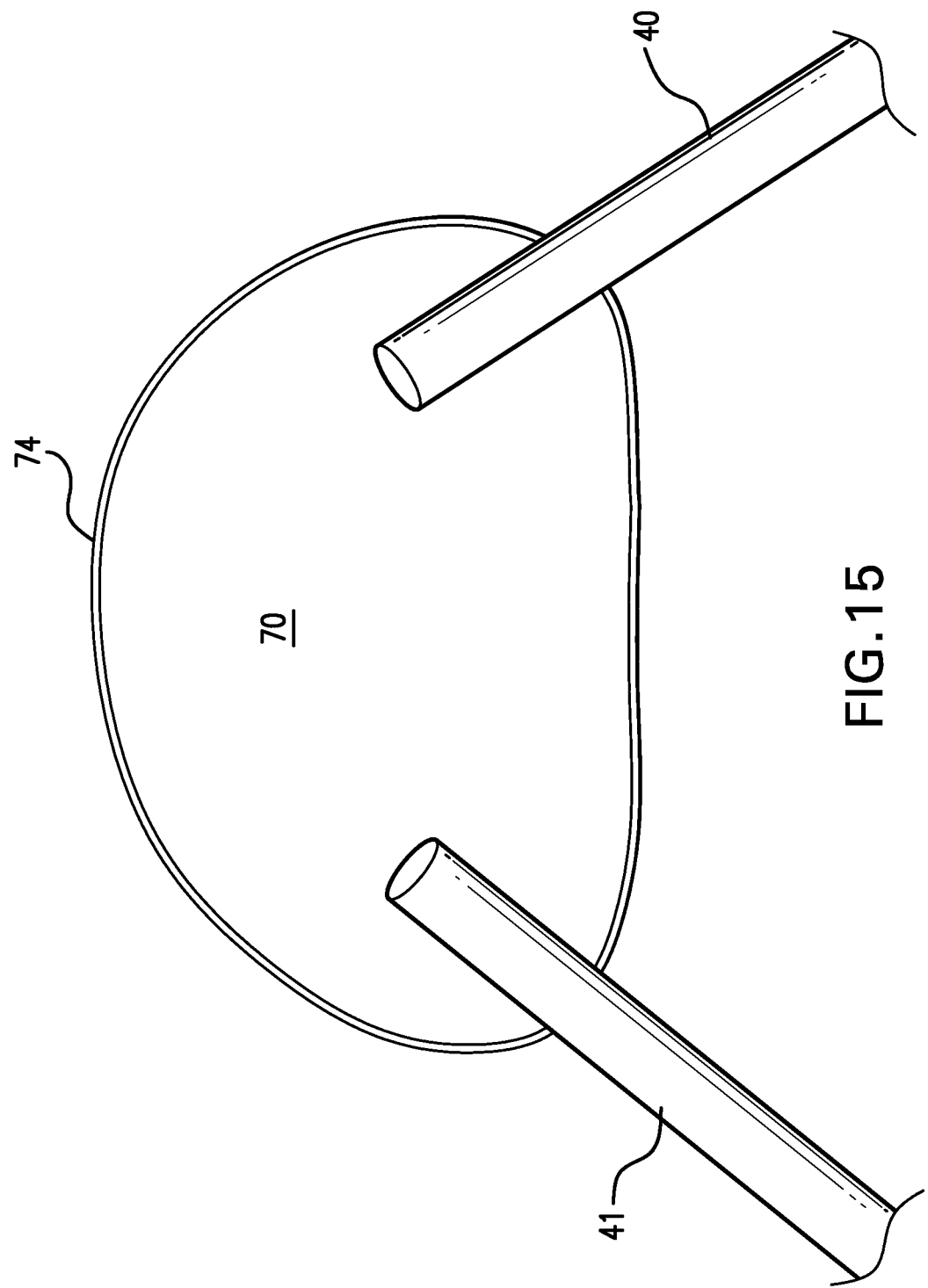
FIG. 15 shows a top cross-sectional view of an intervertebral disc space (i.e., between two vertebral bodies) being accessed by two cannulas in accordance with one embodiment of the present invention.

As shown in FIG. 14, the method may comprise a first step of inserting one or two access members (e.g., cannulas) in, or adjacent to, a body part of interest via percutaneous access 202. The body part may then be accessed. For example, if the body part is a bone, an incision may be cut into the bone. Or, for soft tissue (e.g., an intervertebral disc), the cannula may be positioned so as to abut the tissue of interest. For example, FIG. 15 shows two access cannulas 40, 41 accessing an intervertebral region 70. For orientation, 74 is the anterior (front) of the disc 70.

The user (e.g., a surgeon, veterinarian, or other medical personnel) may then use the access member (e.g., access cannula) to remove any tissue that is to be replaced 204. For example, where the expandable device is used in a spinal fusion procedure, the user may remove any degenerated disc material as is required. In some cases, and as shown in FIG. 14, the removal of tissue may be done, at least in part, before emplacement of a first inflatable member (discussed below). Or, this step may be done before emplacement of the second inflatable member, but after emplacement of the first inflatable member. Or, this step may be done after emplacement of two inflatable members.

Figure 16:
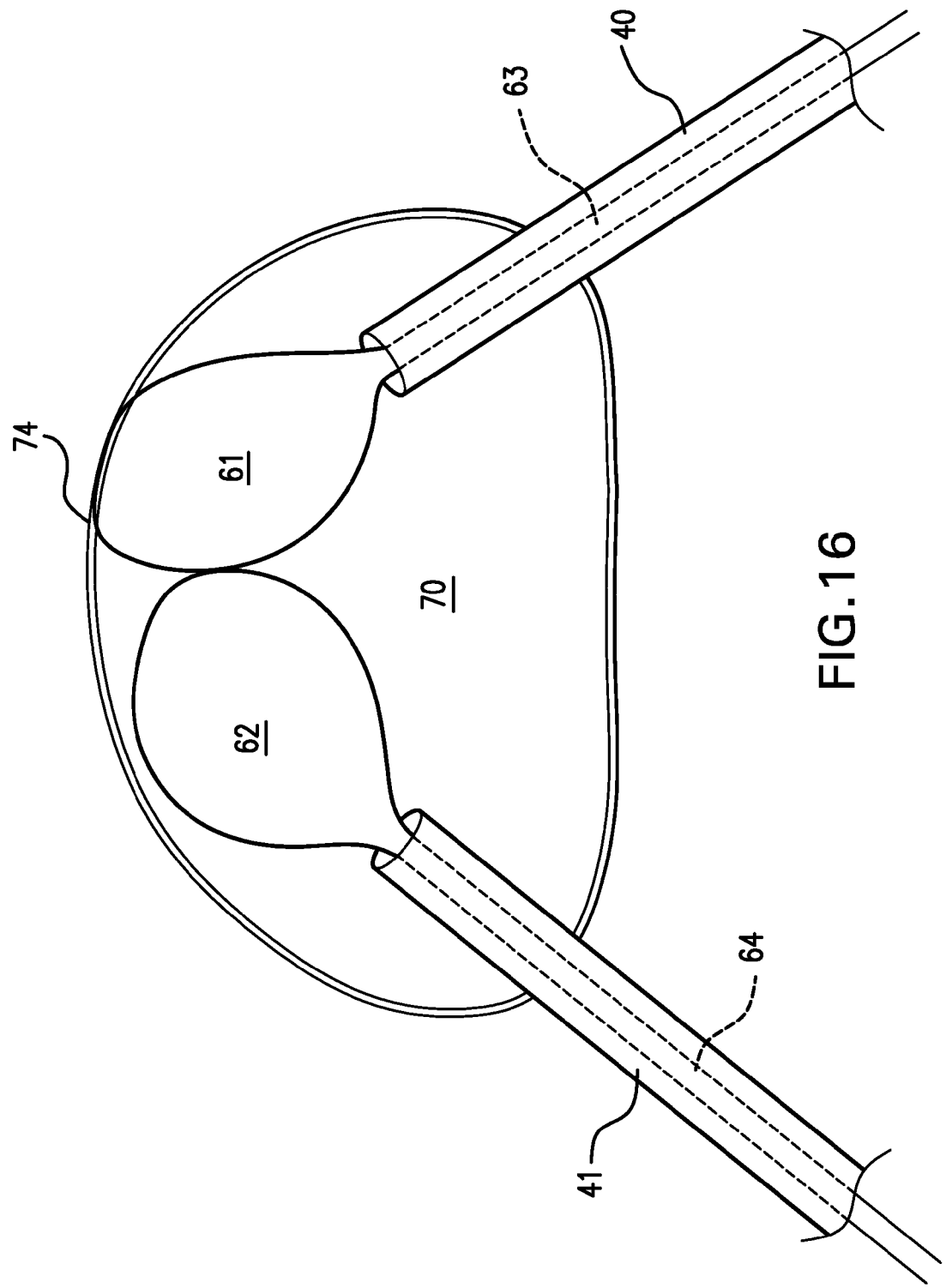
FIG. 16 shows a top cross-sectional view of an intervertebral disc space into which two inflatable members have been emplaced using two cannulas in accordance with one embodiment of the present invention.

Next, an inflatable member or members (e.g., balloons) may be inserted into the body part via the emplaced access cannula or cannulas 206 (FIG. 14). The inflatable member(s) may then be inflated to an extent sufficient to position and support the vertebral bodies in correct alignment. In some cases it may be determined that a second inflatable member is required. In some cases it may be desirable to emplace two inflatable members, each one positioned along the anterior lateral edge of the intervertebral disc space. For example, FIG. 16 shows two inflatable members 61, 62 inserted into an intervertebral disc space (after removal of damaged tissue) and inflated using shafts 63, 64 (e.g., IBT shafts or the like).

Figure 17:
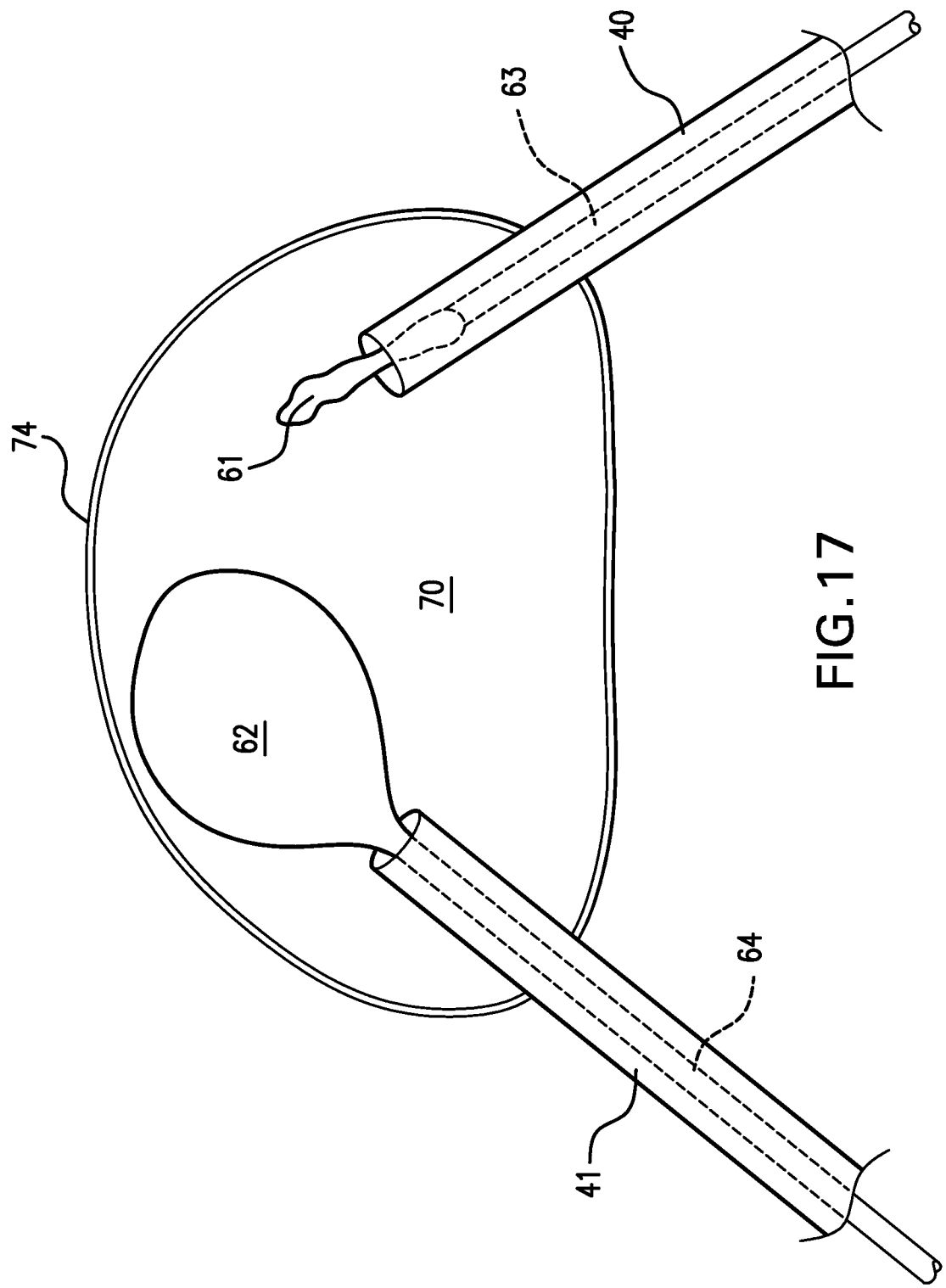
FIG. 17 shows a top cross-sectional view of an intervertebral disc space into which two inflatable members have been emplaced and one inflatable member has been deflated and is being withdrawn using a cannula in accordance with one embodiment of the present invention.

Once the body part has been prepared to receive the expandable device, at least one of the inflatable members may be removed 208 (FIG. 14). For example, as shown in FIG. 17, inflatable member 61 may be deflated, and then withdrawn from the intervertebral disc space 70 by pulling shaft 63 out of the proximal end of access cannula 40. The other inflatable member 62, may remain in place during insertion of an expandable device on one side of the intervertebral disc space. It is to be understood that while the figures illustrate one embodiment of preparing an intervertebral disc space for insertion of an expandable device of the invention, other steps as known in the art may be required for preparation of other body parts to receive the expandable device.

Figure 18:
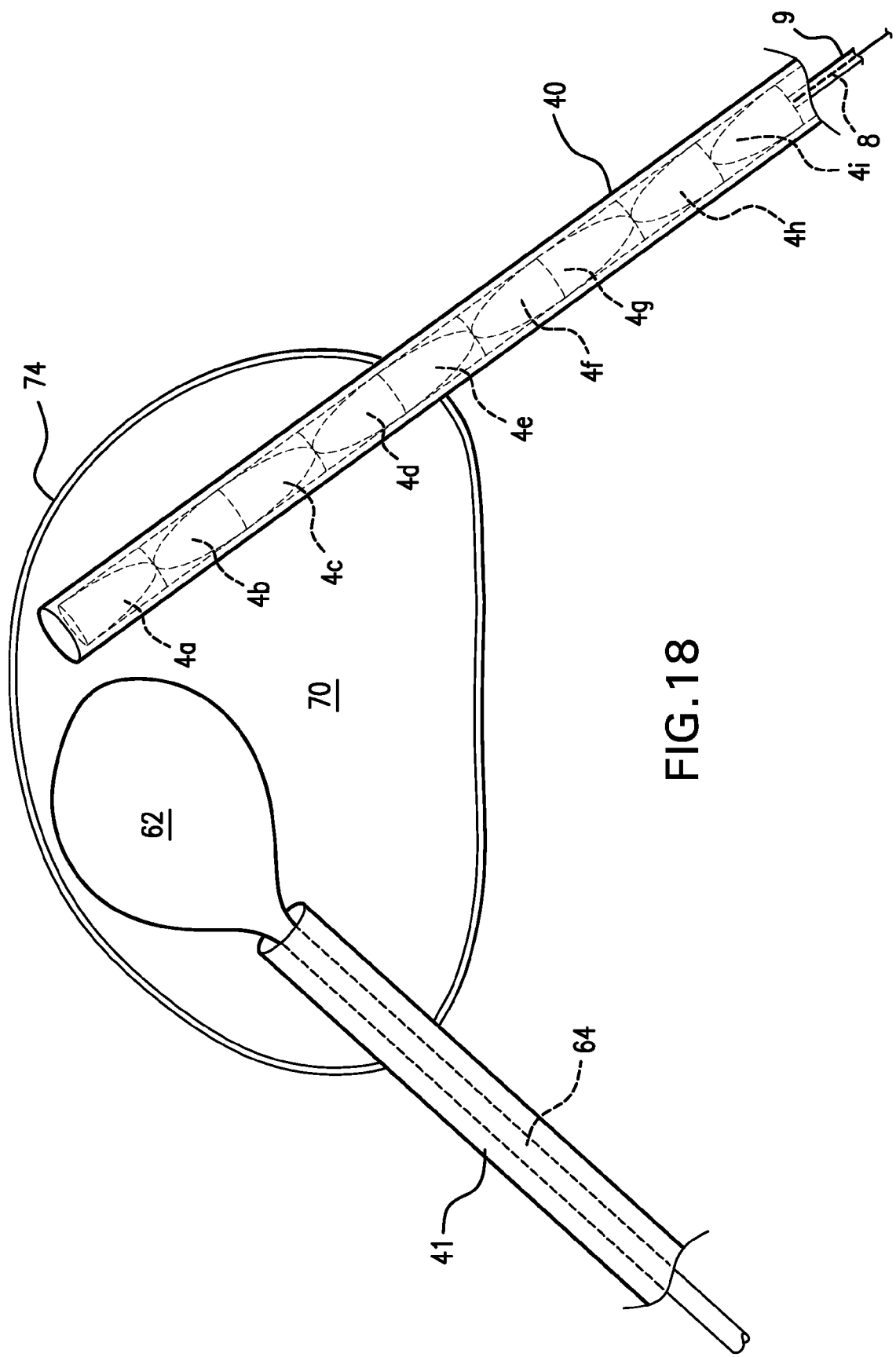
FIG. 18 shows a top cross-sectional view of a first expandable device (e.g., a fusion cage) being delivered to an intervertebral disc space in accordance with one embodiment of the present invention.

Once the body part of interest has been prepared to receive the expandable device, the user may position the expandable device in the body part. For example, in one embodiment, the user may insert the undeployed (i.e., elongated or unfolded) expandable device into the first access cannula. The user may then thread the undeployed expandable device through the cannula until the distal end of the expandable device is positioned at the distal end of the cannula 210 (FIG. 14). At this point, the user may position the distal end of the cannula, and also the distal end of the expandable device, in the anterior region of the intervertebral disc space 212. In one embodiment, the cannula access is extrapedicular, such that the cannula enters the disc space from the side, with its distal end positioned almost at the center of the anterior end of the disc space. FIG. 18 shows an expandable device of the invention comprised of segments 4*a*-4*i* threaded through the access cannula 40, with the distal end of the expandable device and the distal end of the access cannula positioned near the anterior side 74 of the intervertebral space 70. Shown in FIG. 18 is a repositioning member (e.g., wire) 8 which can be pulled to deploy the expandable device and allow vertical expansion of segments 4*a*-4*i*. Also shown in FIG. 18 is pushing member 9 (e.g., a hollow rod or the like) which is used to push the expandable device out of the distal end of the cannula while the repositioning member is being pulled proximally to deploy the expandable device. As shown in FIG. 18, the pushing member 9 can be positioned concentrically to repositioning member 8. Generally, there is no need to connect the pushing member 9 to the expandable device since it will function by being pushed against the proximal end of the undeployed expandable device.

The user may then push the expandable device out of the cannula by pushing the expandable device towards the distal end of the cannula while pulling the repositioning member such that the segments deploy upon exiting the cannula 214 (FIG. 14). Or, in certain embodiments, the device may comprise segments that are connected such that the segments are biased towards the second configuration as for example, where the hinges or repositioning members comprise spring-like elements. Or, the user may allow the majority or all of the segments to exit the cannula prior to urging the device to the second configuration (i.e., deploying or folding the device).

Figure 19:
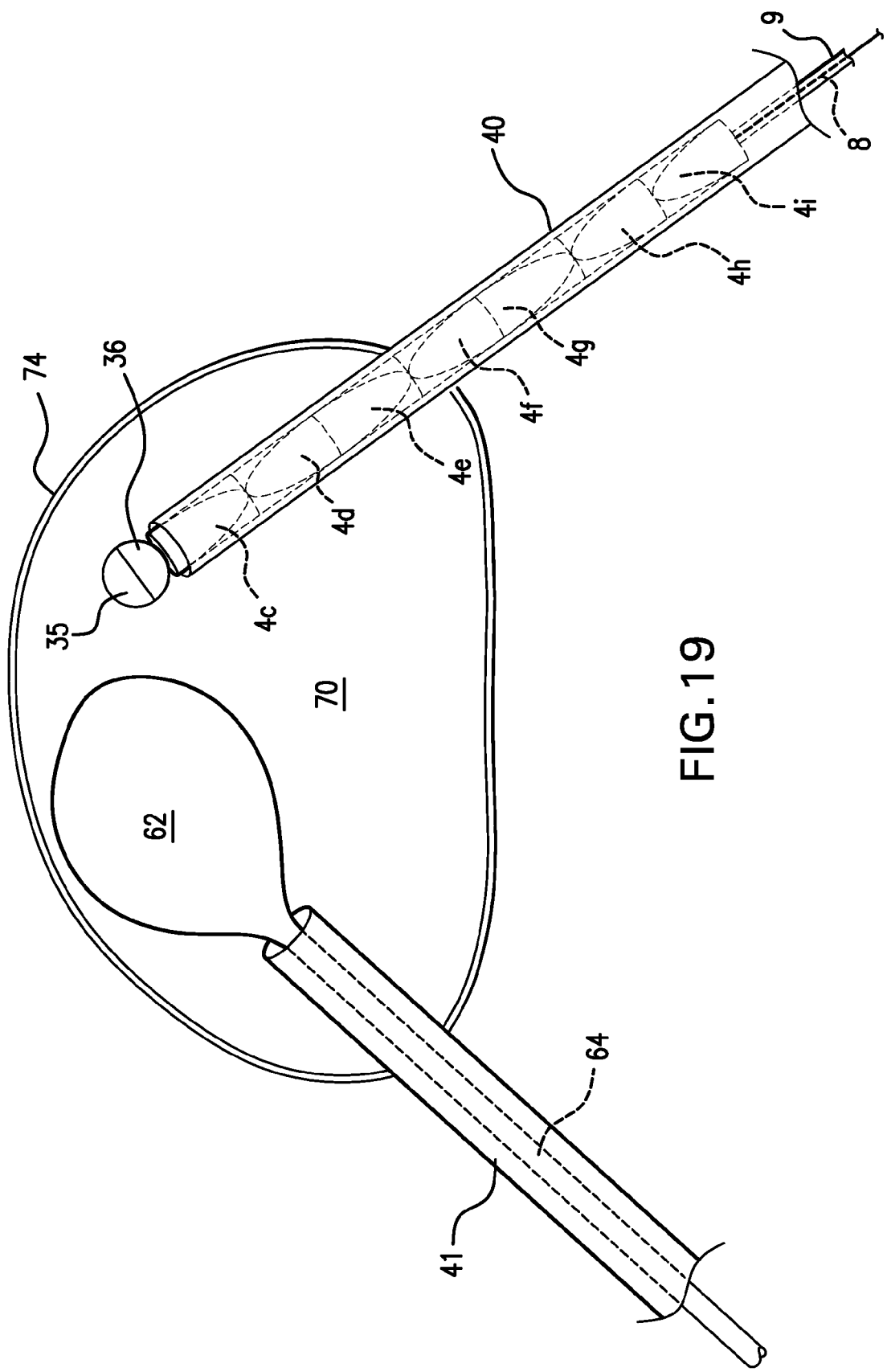
FIG. 19 shows a top cross-sectional view of a first expandable device that is partially deployed in an intervertebral disc space in accordance with one embodiment of the present invention.

FIG. 19 shows an embodiment in which the expandable device is beginning to be deployed or folded in the intervertebral disc space 70. It can be seen that the expandable device may be pushed out of the cannula 40 by pushing the expandable device towards the distal end of the cannula and thus, towards the anterior 74 of the intravertebral disc space, as for example, using pushing member 9, while pulling the repositioning member 8 towards the proximal end of the cannula such that at least two segments 4a, 4b vertically deploy upon exiting the cannula 40. In this way, the upper surface of the expandable device will abut the lower surface of the upper vertebral body and the lower surface of the expandable device will abut the upper surface of the lower vertebral body.

Figure 20:
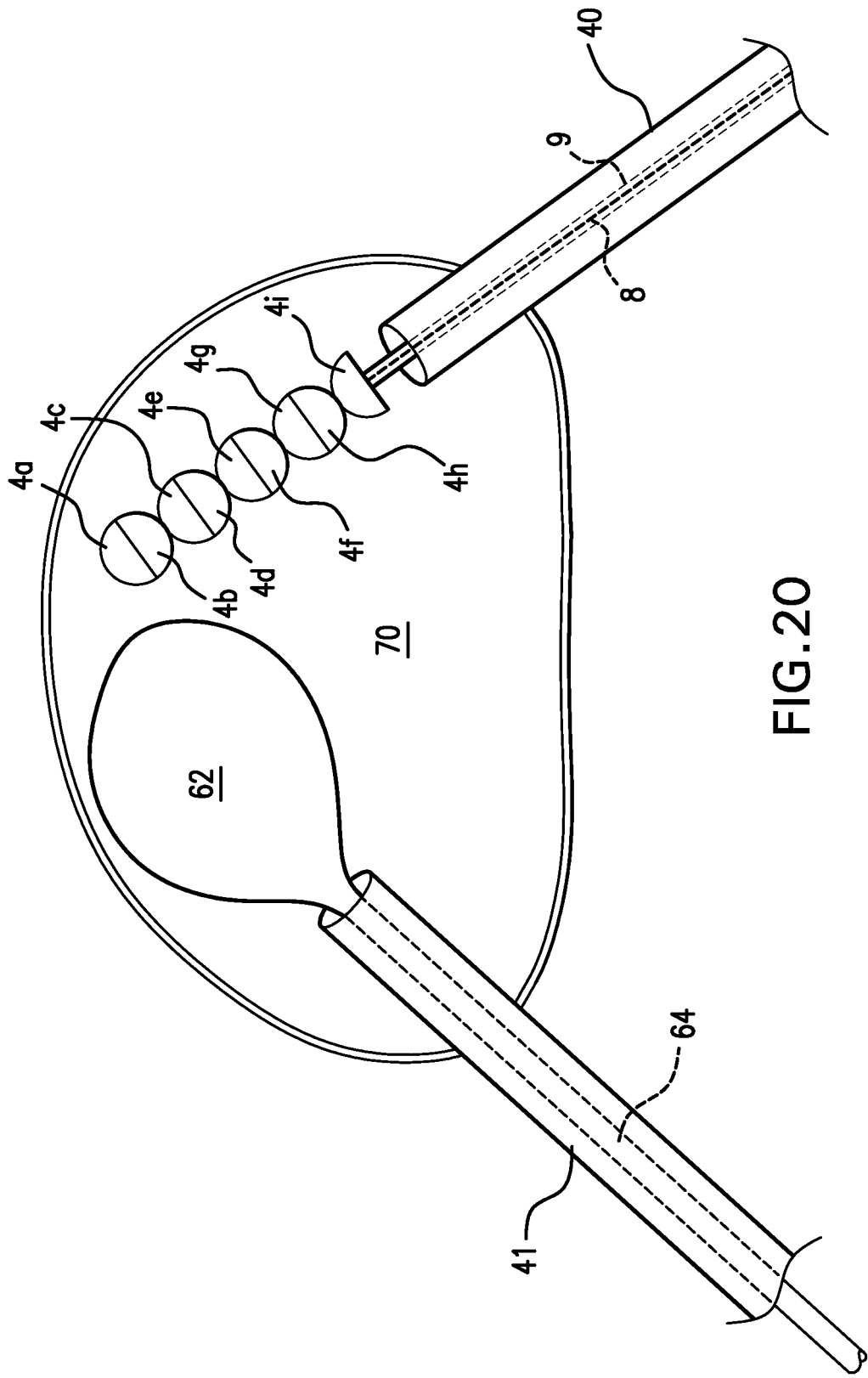
FIG. 20 shows a top cross-sectional view of a first expandable device that is fully deployed in an intervertebral disc space in accordance with one embodiment of the present invention.

The user may then continue to push the expandable device out of the cannula while pulling on the repositioning member until the entire expandable device is deployed 216 (FIG. 14). FIG. 20 shows an embodiment where an expandable device of the invention has completely exited the cannula 40 and been folded or deployed such that each of the segments are now engaged at adjacent longitudinal surfaces. At this point, the expandable device may be disengaged from the repositioning member 8 and the deployment rod 9. For example, the tensioning wire may be hooked onto the proximal end of the expandable device (e.g., 4i in FIG. 20) by a hook type clasp or other releasable connector, such that the wire may be disengaged from the expandable device by an operator manipulating the proximal end of the wire. In an embodiment, the wire can be disengaged by first being pulled tight. A crimp or ferrule can then be crimped at the longitudinal face of the most proximal segment to maintain tightness of the assembly. Finally, the excess wire may be cut just proximal to the crimp using any of a plurality of wire cutting devices. As noted herein, the pushing member is generally not connected to the expandable device and so may simply be withdrawn out of the cannula 40.

Figure 21:
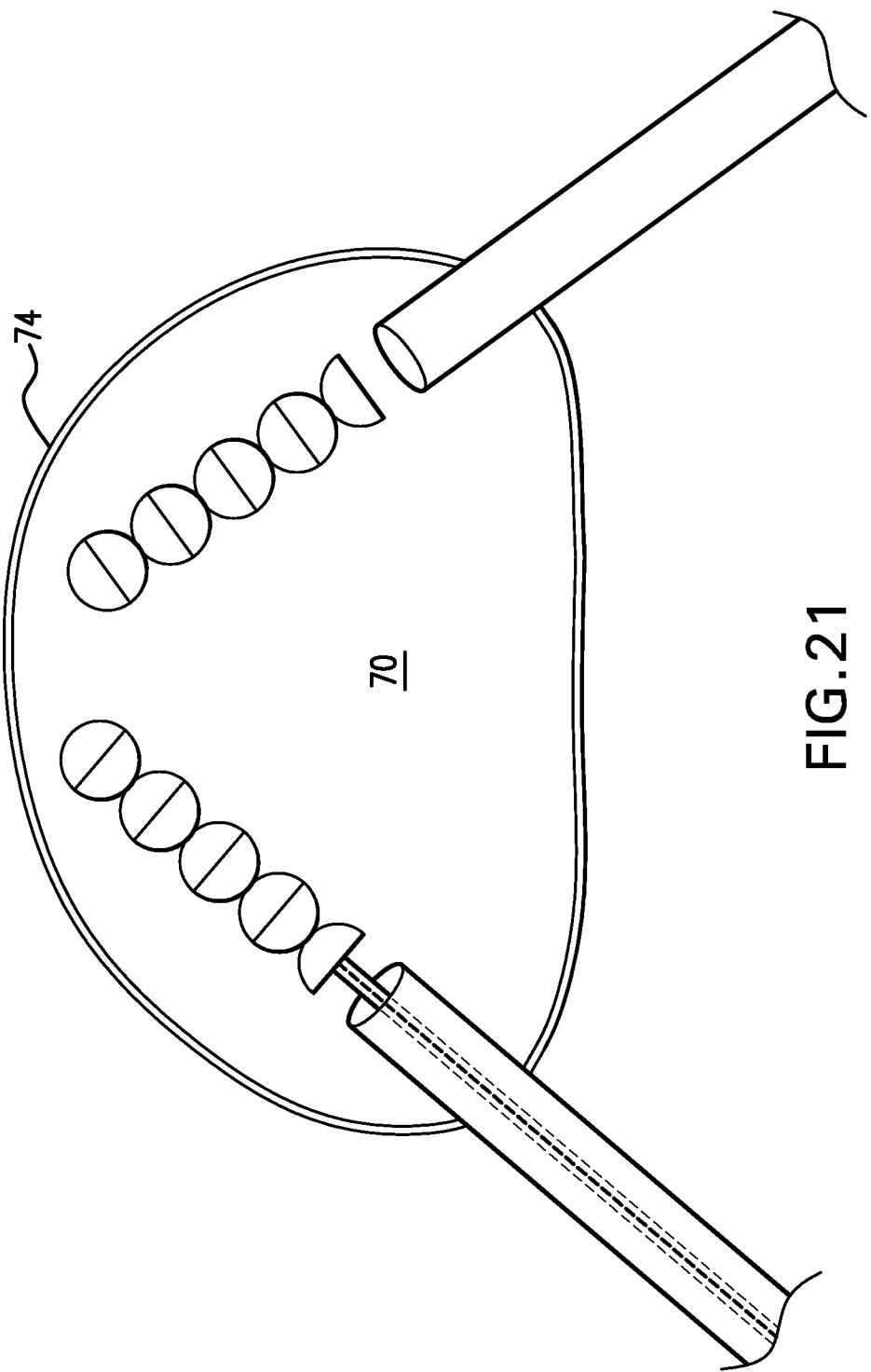
FIG. 21 shows a top cross-sectional view of two expandable devices that are fully deployed in an intervertebral disc space in accordance with one embodiment of the present invention.

In some cases, a plurality of expandable devices may be emplaced. If needed, the user may deploy another expandable device in the body part of interest. For example, the user may deploy anther expandable device on the other side of the intervertebral disc space. Thus, as shown in FIG. 14, the user may then deflate and remove the other inflatable member 218, and insert a second expandable device at another position in the body part to be repaired 220 by repeating steps used to insert the first expandable device. For example, for an intervertebral disc, a second expandable device may be emplaced in the other side of the disc space. FIG. 21 shows an intervertebral disc space with two expandable devices emplaced, and the repositioning members and pushing members 8, 9, removed from one of the cannulas.

Figure 22:
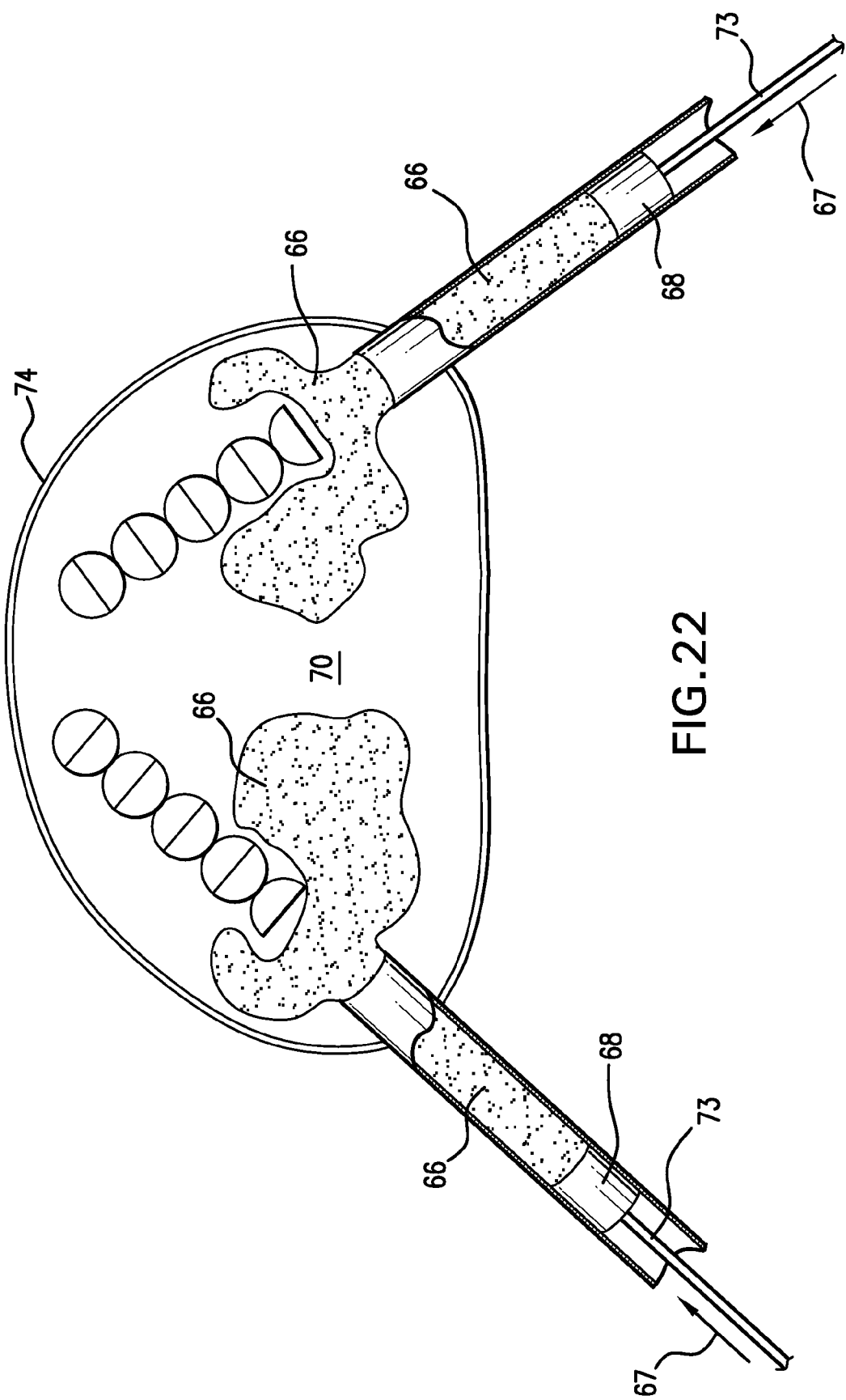
FIG. 22 shows a top cross-sectional view of two expandable devices deployed in an intervertebral disc space and the emplacement of biological graft material at least part of in the remaining void in accordance with one embodiment of the present invention.

In some cases, a therapeutic agent is emplaced in the body part of interest. For example, the method may further comprise emplacing a bone graft material to promote fusion of a vertebral body that is adjacent to an upper surface of the deployed expandable device to a vertebral body that is adjacent to a lower surface of the deployed expandable device after the device has been emplaced. Thus, using one or both access cannulas, the user may emplace a bone graft material into any voids that remain in the body part 222 (FIG. 14). FIG. 22 shows a bone graft material 66 being emplaced into a disc space into which two expandable devices of the invention have been deployed. For example, the therapeutic agent 66 may be urged into the body part of interest using a plunger 68 and pushing 67 the material out the distal end of the cannula(s) 40, 41 using a rod 73 attached to the plunger 68.

Once the bone graft material has been emplaced, the access cannula(s) and remaining tools used for the procedure may be removed 224 (FIG. 14). The bone graft material may then grow, thereby filling in any voids remaining in the body part of interest. For example, for a spinal fusion, the bone graft material will fill in the intervertebral space, thereby allowing fusion of the lower and upper vertebral bodies.

Systems and Kits

In other embodiments, the present invention comprises systems and kits comprising an expandable device for emplacement in a body part. In certain embodiments, the systems of kits of the present invention comprise (a) an expandable device comprising a plurality of segments, the plurality of segments being flexibly connected in series, the expandable device having a first configuration wherein the plurality of segments are substantially unfolded, and a second configuration wherein the plurality of segments are substantially folded, and wherein a total height of the expandable device in the second configuration is substantially spanned by at least one of the plurality of segments; and (b) an access member for inserting the device into the body part of interest. In some embodiments, the access member may comprise a cannula. Also, in some embodiments, the kit may comprise instructions for use.

In some embodiments, the plurality of longitudinal axes of the plurality of connected segments are substantially co-axial in the first configuration. The plurality of segments may be folded in alternating directions in the second configuration. Also in some embodiments, the plurality of longitudinal axes of the plurality of connected segments are substantially parallel. For example in certain embodiments, a longitudinal surface of a first one of the plurality of connected segments is substantially flush with a longitudinal surface of a second one of the plurality of connected segments in the second configuration. For example, in some embodiments, the systems or kits of the present invention comprise an expandable device for emplacement in a body part in a subject comprising a first member comprising a plurality of segments that may fold in a coordinated manner from a first configuration in which the segments are aligned such that an axial end of each segment is substantially flush with an axial end of an adjacent segment, to a second configuration wherein a longitudinal surface of at least one segment is substantially flush with a longitudinal surface of a second, adjacent segment. The segments may be separate parts, or the segments may be joined together as a single unit. In one embodiment, the segments are each connected to at least one other of the plurality of segments. For example, in one embodiment the segments are connected to each other by a hinge between adjacent segments. In certain embodiments, the plurality of connected segments are connected by a plurality of hinges, each of the plurality of hinges having a thickness less than a thickness of each of the plurality of connected segments. For example, in some embodiments, the plurality of connected segments are connected by living hinges.

In other embodiments, the device of the systems and kits comprises a repositioning member for urging the first member between the first configuration and the second configuration. The repositioning member may engage each of the segments. In some embodiments, the repositioning member may engage each of the segments, such that the repositioning member can be used by an operator of the device to urge the segments from the first configuration to the second configuration, or from the second configuration to the first configuration. In one embodiment, the repositioning can be loosened to allow the segments to be positioned such that the segments are substantially unfolded (e.g., having an axial end of each segment substantially flush with an axial end of an adjacent segment), or the connector can be tightened such that the segments are substantially folded (e.g., having a longitudinal surface of at least one segment substantially flush) with the longitudinal surface of a second segment.

In certain embodiments, the repositioning member used in the device of the systems and kits of the present invention may comprise a wire that is passed through at least one aperture on each of the segments. The wire may pass through the segments in an alternating manner. For example, the wire may loop through an aperture positioned in each of the segments in a manner so as to extend from a first segment to a second segment on one face of the unit (e.g., upper or superior) and then to extend from the second segment to the third segment on the opposite face of the unit (e.g., lower or inferior). The wire may then extend from the third segment to the fourth segment on the superior face, and from the fourth segment to the fifth segment on the inferior face, and so forth, until all of the segments are connected.

The positioning of the wire relative to the upper and lower faces of the unit may allow for the wire to function so as to collapse the upper and lower faces (i.e., longitudinal surfaces) of the segments together such that the longitudinal surfaces of adjacent segments go from a substantially unfolded or linear arrangement to an arrangement where the longitudinal surfaces of adjacent segments are substantially folded together. Thus, in one embodiment, the wire is fixedly attached to a segment positioned on one end of the device such that the when the connector is pulled toward the other segments, the adjacent segments are pulled towards each other such that the longitudinal surface of one segment is urged to a final configuration in which it is substantially flush with the longitudinal surface of a second segment.

The segments may also comprise elements to assist in the alignment of the segments when the longitudinal surfaces of at least two segments are substantially flush. In this way, the tendency of the segments to twist off center and become misaligned can be reduced. For example, in one embodiment, the alignment elements may comprise at least one protrusion on a first segment and at least one aperture to receive the pin on an adjacent segment. Or, multiple protrusions and apertures may be used. Generally, each of the longitudinal surfaces may comprise at least two protrusions and receiving apertures. For example, in one embodiment, the protrusions and receiving apertures are positioned close to the axial end of each segment. In this way, when each protrusion and aperture interlock, the mating will prevent the two segments from twisting relative to the longitudinal (i.e., longest) axis of the longitudinal surface.

Figure 23:
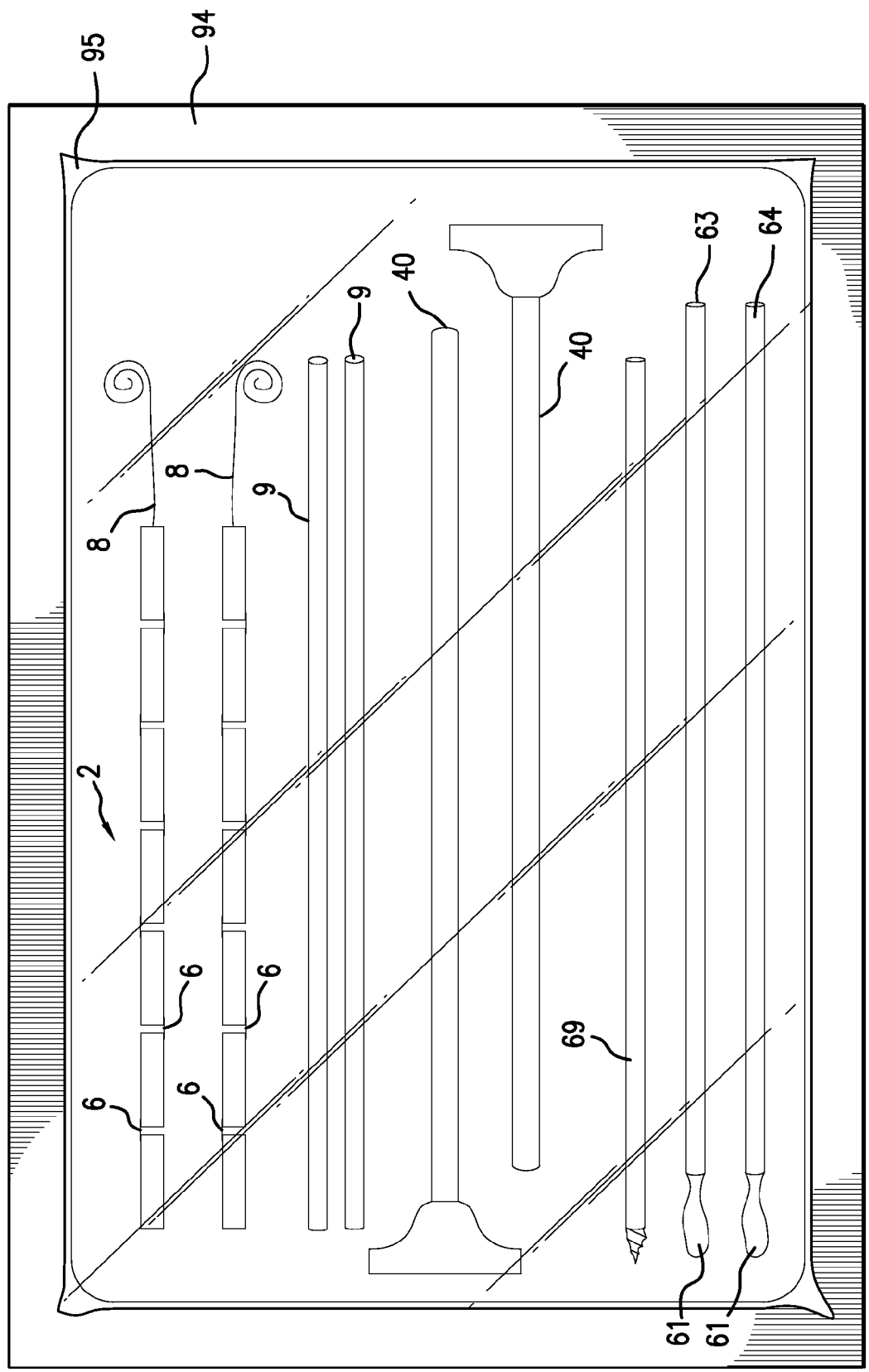
FIG. 23 shows a kit that includes expandable devices in accordance with one embodiment of the present invention.

FIG. 23 shows an illustration of one embodiment of a kit of the present invention. Thus, as shown in FIG. 23, the kit may comprise one or more expandable devices 2 having segments that are connected by hinges 6. In some embodiments, the expandable device further includes a repositioning member 8 that is used to urge the segments between the first configuration and the second configuration. The kit may also include an access member 40, or multiple access members, such as a cannula for inserting the device into a body part. The kit may further comprise a pushing member 9, or multiple pushing members for urging the expandable device through the cannula.

The kit and systems of the present invention may also include inflatable members. For example, in certain embodiments, the kits and systems may be used to emplace an inflatable member into the body part to support the body part during emplacement of the expandable device. Also, a plurality of inflatable members 61, 62 may be included. In one embodiment, the inflatable members may comprise balloons, such as those used in kyphoplasty. Or, other inflatable members may be used. The kit may also include other tools or devices needed for access of the body part as for example, drills 69 or other types of percutaneous access devices.

In certain embodiments of the systems and kits of the present invention, the segments are configured for percutaneous delivery to a body part using a cannula. Expandable devices of the present invention may be designed for emplacement in a variety of body parts. For example, the expandable devices may be emplaced in a boney structure, or between two bones. In one embodiment, the expandable device may be emplaced between two vertebral bodies, to replace the intervertebral disc. The systems and kits of the present invention allow the treatment of any vertebrae; for example, the expandable device can be applied to pelvic, lumbar, thoracic, or cervical vertebrae. Where the expandable device is emplaced between two vertebral bodies, the access may be extrapedicular, transpedicular or anterior. For example, where the expandable device is emplaced between two vertebral bodies as part of a bone graft procedure, the kits and systems of the present invention may comprise emplacing a bone graft material to promote fusion of the vertebral bodies.

The kits and systems of the present invention may, in certain embodiments, include a bone graft material or other biological materials required for the procedure of interest. In certain embodiments, the kit may comprise a bone graft material for emplacement in an intervertebral disc space to promote fusion of a vertebral body that is adjacent to an upper surface of the deployed expandable device to a vertebral body that is adjacent to a lower surface of the deployed expandable device. For example, the bone graft material of the present invention may include allograft, autograft, BMP (bone-morphogenic proteins), bone marrow aspirate, demineralized bone matrix, ceramics, calcium phosphates, blood platelet gels, and other similar and known materials that are suitable for bone grafts. The kit may include an outer wrap and/or a case 94 to protect the components of the system from physical damage. Also, the kit may further include an inner wrap 95 which, in certain embodiments, may be sealed by heat or vacuum to prevent the components of the kit from being exposed to the outside environment. The inner/outer wraps may be made of wrap materials commonly used in the art such as polyethylene, TYVEK™, or MYLAR™, to allow for visualization of the components in the kit and or sterilization using a sterilizing gas. Sterilization may be by heat, pressure and/or sterilization gas as is known in the art. Also, the kit may include directions for use by a physician, veterinarian, or other trained personnel.

Each of the components used in the products, systems, and kits of the present invention may comprise a material that may be sterilized by either chemical treatment, high temperature, and/or high pressure, exposure to sterilizing gas, or a combination of sterilization treatments as is known in the art. Also, the components of the products, systems, and kits of the present invention may be disposable, or may be formulated to allow for cleaning, re-sterilization, and re-use.

Methods of Making

The present invention also includes methods of making an expandable device for emplacement in a body part. In one embodiment, the method may comprise fashioning a first member comprising a plurality of segments. In one embodiment, the present invention comprises a method of making an expandable device for emplacement in a body part comprising fashioning a plurality of connected segments, the plurality of connected segments being flexibly connected in series, the expandable device having a first configuration wherein the plurality of segments are substantially unfolded, and a second configuration wherein the plurality of segments are substantially folded, and wherein a total height of the expandable device in the second configuration is substantially spanned by at least one of the plurality of segments.

In some embodiments, the plurality of longitudinal axes of the plurality of connected segments are substantially co-axial in the first configuration. The plurality of segments may be folded in alternating directions in the second configuration. Also in some embodiments, the plurality of longitudinal axes of the plurality of connected segments are substantially parallel. For example in certain embodiments, a longitudinal surface of a first one of the plurality of connected segments is substantially flush with a longitudinal surface of a second one of the plurality of connected segments in the second configuration. For example, the method may comprise fashioning a first member comprising a plurality of segments that may fold in a coordinated manner from a first configuration in which the segments are aligned such that an axial end of each segment is substantially flush with an axial end of an adjacent segment, to a second configuration wherein a longitudinal surface of at least one segment is substantially flush with a longitudinal surface of a second, adjacent segment.

In one embodiment, the segments are each connected to at least one other of the plurality of segments. In certain embodiments, the plurality of connected segments are connected by a plurality of hinges, each of the plurality of hinges having a thickness less than a thickness of each of the plurality of connected segments. For example, in some embodiments, the plurality of connected segments are connected by living hinges.

The first member may be fashioned as a single piece. For example, in one embodiment, the first member may be injection molded plastic, such as PEEK, ultra high molecular weight polyethylene, or polycarbonate. The living hinge may be fashioned as a very thin connection between adjacent segments. Or, the living hinge may be molded from a metal such as NITINOL or steel. For example, in some embodiments, the living hinge comprises a spring-like material that biases the segments in the second configuration. As seen in FIG. 1, the device may be fashioned such that the hinges are on opposite sides for each of the adjacent segments. For example, as illustrated in the embodiment shown in FIG. 1, if the hinge between the first segment 4a and the second segment 4b is positioned on the lower (inferior) surface, then the hinge between the second segment 4b and the third segment 4c will be positioned on the upper (superior) surface, and the hinge between the third segment 4c and the fourth segment 4d will be positioned on the lower surface and so forth. In this way, bending of the segments at the hinges can occur during deployment to allow for vertical expansion.

The method may also comprise fashioning a repositioning member that engages each of the segments such that the repositioning member can be used to urge the expandable device between the first configuration and the second configuration. The repositioning member may, in certain embodiments, engage each of the segments, such that the repositioning member can be used by an operator of the device to urge the segments from the first configuration to the second configuration, or from the second configuration to the first configuration. In one embodiment, the repositioning member is fashioned such that it can be loosened to allow the segments to unfold and be tightened to allow the segments to fold. In one embodiment, the repositioning member is used to urge the device from a first configuration such that the axial end of one segment is substantially flush with an axial end of an adjacent segment to a second configuration such that the longitudinal surface of one segment is substantially flush with the longitudinal surface of a second segment. Or, the repositioning member may comprise a spring-like material that biases the segments in the second configuration.

In an embodiment, the repositioning member comprises a wire that is passed through at least one aperture on each of the segments. The wire may be fixedly attached to a segment at one end of the device. The wire may pass through the segments in an alternating manner. For example, the wire may be fixedly attached to the most distal segment (4a) and then loop through an aperture positioned in each of the segments in a manner so as to extend from a first segment (e.g., 4a) to a second segment (e.g., 4b) on one face of the unit (e.g., upper or superior) and then to extend from the second segment to the third segment on the opposite face of the unit (e.g., lower or inferior). The wire may then extend from the third segment to the fourth segment on the superior face, and from the fourth segment to the fifth segment on the inferior face, and so forth, until all of the segments are connected.

The positioning of the wire relative to the upper and lower faces of the unit allows for the wire to function so as to collapse the upper and lower faces (i.e., longitudinal surfaces) of the segments together such that the longitudinal surfaces of adjacent segments go from a substantially unfolded or linear arrangement, to an arrangement where the longitudinal surfaces of adjacent segments are substantially folded together. Thus, in one embodiment, the wire is fixedly attached to a segment positioned on one end of the device such that the when the connector is pulled toward the other segments, the adjacent segments are pulled towards each other and the longitudinal surface of one segment is urged to a final configuration in which it is substantially flush with the longitudinal surface of a second segment. In one embodiment, the connector may be pulled such that it is completely tightened (i.e., can be pulled no further). At this point, the device will have a configuration such that at least one surface of each segment is substantially flush with at least one surface of an adjacent segment.

In alternate embodiments, the repositioning member may be made of titanium, stainless steel or NITINOL (i.e., a nickel titanium alloy). It should be understood that for either the segments or the repositioning member, other materials are contemplated such as of PEEK (polyetheretherketones) ultra high molecular weight polyethylene, nylon or polycarbonate, silicone and metal materials, tantalum, platinum, titanium, and niobium alloys, PHYNOX®, or any of a plurality of polymeric materials, such as polytetrafluoroethylene (ePTFE). Alternatively, the repositioning member may be made of any one of tungsten, iridium platinum, ELGILOY (Elgin, Ill.), or mixtures thereof or any other available metal alloy suitable for its intended purpose.

As discussed herein, when fully deployed, the expandable device of the present invention will have a height that is equal to the longitudinal length of each segment. The method may therefore comprise fashioning elements on the individual segments to assist in the alignment of the segments when the longitudinal surfaces of at least two segments are substantially flush. In this way, the tendency of the segments to twist off center and become misaligned can be reduced. For example, in one embodiment, the alignment elements may comprise at least one pin fashioned on a first segment and at least one aperture to receive the pin fashioned on an adjacent segment. Or, multiple pins and apertures may be used. Generally, each of the longitudinal surfaces may comprise at least two pins and receiving apertures. For example, in one embodiment, the pins and receiving apertures are positioned close to the axial end of each segment. In this embodiment, the male fixtures may comprise pins, plugs, or other types of male fixtures. The apertures may be made during the molding process or cut into an already molded segment.

In certain embodiments of the present invention, the segments are configured for percutaneous delivery to a body part using a catheter. Expandable devices of the present invention may be designed for emplacement in a variety of body parts. For example, the expandable devices may be fashioned to have a size and shape for emplacing in a boney structure, or between two bones. In one embodiment, the expandable device may be emplaced between two vertebral bodies, to replace the intervertebral disc. The systems and kits of the present invention allow the treatment of any vertebrae, for example, the expandable device can be applied to pelvic, lumbar, thoracic, or cervical vertebrae.

In one embodiment, the expandable device is configured to have a substantially rectangular shape when the expandable device is deployed. In this embodiment, the side walls may be arcuate such that the expandable device, when in its undeployed state, has an outer surface that generally cylindrical. In this way, the expandable device can be deployed via a cylindrical access member, such as a cylindrical cannula. It should be understood that in the embodiment where the expandable device is used to replace an intervertebral disc for a spinal fusion, the shape of the expandable device can be any shape that will provide the needed positioning and stabilizing of the vertebrae during the fusion procedure and after the administration of the agent used to promote fusion.

The size of the segments and the number of segments used may depend on the body part for which the expandable device is to be used. For example, for use in spinal fusions, in alternate embodiments the segments that comprise the expandable device range from between about 0.3 to 2.0, or 0.6 to 1.0 cm in height, 0.3 to 2.0 to 0.6 to 1.0 cm in width, and 1.0 to 8, or 2.0 to 5.0 cm in length. The expandable device dimensions may be varied such that the expandable device has dimensions suitable for placement between the vertebrae of a normal sized adult patient. However, it should be understood that other sizes are contemplated and therefore within the scope of the invention, for example, when the expandable devices are used on children or on adults that are of smaller or larger stature.

The expandable device may comprise any number of segments depending upon the body part into which the expandable device is to be inserted. Also, the segments may vary with respect to the relative ratio between of the diameter (or width and/or height of the segment) as compared to the length. In alternate embodiments, the length of each segment is about 1.5 to 10, or 1.2 to 5, or 2 to 3 times the diameter (or width and/or height) of the segment.

Other materials/chemicals may be associated with the expandable device of the present invention such as lubricants, antibiotics, anti-cancer agents, bone cements, bone grafts, chemicals that prevent autoimmune defenses, and the like. In an embodiment, these materials/chemicals may be released over an extended time period. These materials/chemicals may be used to aid accretion of bone or of tissue, to aid in fighting off bacterial infections, to promote tissue growth or for a plurality of other reasons. Such agents may be coated onto the expandable device, or attached as time-release capsules or by other means known in the art.

It will be understood that each of the elements described above, or two or more together, may also find utility in applications differing from the types described. While the invention has been illustrated and described as devices, systems, kits and methods for emplacing an expandable device in an internal body part, it is not intended to be limited to the details shown, since various modifications and substitutions can be made without departing in any way from the spirit of the present invention. Where method and steps describe above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. As such, further modifications and equivalents of the invention herein disclosed may occur to persons skilled in the art using no more than routine experimentation, and all such modifications and equivalents are believed to be within the spirit and scope of the invention as described herein. All patents and published patent applications referred to in this document are incorporated by reference in their entireties as if each individual publication or patent application were specifically and individually put forth herein.

That which is claimed is:

1. An expandable device for emplacing in a body part in a subject comprising:
   a plurality of segments each segment having upper and lower surfaces, at least two longitudinal surfaces disposed between the upper and lower surfaces that are substantially parallel to each other and two axial ends disposed between the upper and lower surfaces and between the longitudinal surfaces that are substantially parallel to each other, the axial ends being disposed in a transverse orientation to the at least two longitudinal surfaces, each segment including an aperture extending through the upper and lower surfaces, the plurality of segments being flexibly connected in series, the expandable device having a first configuration wherein the plurality of segments are substantially unfolded, and a second configuration wherein the plurality of segments are substantially folded, and
   a repositioning member for connecting the segments and positioning the segments between the first and second configurations, wherein the repositioning member extends through the apertures in the segments, wherein an attachment element coupled an end of the repositioning member is positioned in the aperture of one of the segments such that pulling the repositioning member toward the other segments pulls adjacent segments towards each other,
   wherein in the first configuration, the axial end of one segment engages the axial end of an adjacent segment, and in the second configuration the upper surface of one segment engages the upper surface of an adjacent segment.

2. The device of claim 1, wherein in the second configuration, the plurality of segments are folded in alternating directions.

3. The device of claim 1, wherein in the first configuration, a plurality of longitudinal axes of the plurality of segments are substantially co-axial.

4. The device of claim 1, wherein in the second configuration, plurality of longitudinal axes of the plurality of segments are substantially parallel.

5. The device of claim 1, wherein the plurality of segments are connected by a plurality of hinges, each of the plurality of hinges having a thickness less than a thickness of each of the plurality of segments.

6. The device of claim 5, wherein the plurality of hinges biases the plurality of segments towards the second configuration.

7. The device of claim 1, wherein the plurality of segments are connected by living hinges.

8. The device of claim 1, wherein the repositioning member comprises a wire.

9. The device of claim 1, further comprising elements to assist in the alignment of the segments when the device is in the second configuration.

10. The device of claim 1, wherein the body part comprises a spinal disc or an intervertebral region between two vertebral bodies.

11. The device of claim 1, wherein the lower surface of at least one of the segments engages the lower surface of an adjacent segment when the segments are in the second configuration.

12. The device of claim 1, wherein the repositioning member passes through the segments in an alternating manner.

13. The device of claim 1, wherein the repositioning member engages the upper surfaces of two adjacent segments and then extends from one of the two adjacent segments to a third segment adjacent one of the two adjacent segments such that the repositioning member engages the lower surface of the third segment and passes through the two adjacent segments and the third segment in an alternating manner.

14. The device of claim 1, wherein each of the segments includes a second aperture extending through the upper and lower surfaces adjacent the aperture, and at least one of the upper and lower surfaces of a respective segment includes a protrusion configured for disposal in the second aperture of an adjacent segment when the segments are in the second configuration.

15. The device of claim 1, wherein the attachment element is spherical and has a maximum diameter that is greater than that of the respective one of the apertures.

16. A kit comprising an expandable device for emplacement in a body part comprising:
(a) an expandable device comprising a plurality of segments, each segment having upper and lower surfaces, at least two longitudinal surfaces disposed between the upper and lower surfaces that are substantially parallel to each other and two axial ends disposed between the upper and lower surfaces and between the longitudinal surfaces that are substantially parallel to each other, the axial ends being disposed in a transverse orientation to the at least two longitudinal surfaces, each segment including an aperture extending through the upper and lower surfaces, the plurality of segments being flexibly connected in series, the expandable device having a first configuration wherein the plurality of segments are substantially unfolded, and a second configuration wherein the plurality of segments are substantially folded, and a repositioning member for connecting the segments and positioning the segments between the first and second configurations, wherein the repositioning member extends through the apertures in the segments, wherein an attachment element coupled to an end of the repositioning member is positioned in the aperture of one of the segments such that pulling the repositioning member toward the other segments pulls adjacent segments towards each other; wherein in the first configuration, the axial end of one segment engages the axial end of an adjacent segment, and in the second configuration an upper surface of one segment engages the upper surface of an adjacent segment, and
(b) a cannula for inserting the device into the body part of interest.

17. The kit of claim 16, wherein the plurality of connected segments are connected by living hinges.

18. The kit of claim 16, wherein the segments are configured for percutaneous delivery to a body part using the cannula.

19. The kit of claim 16, further comprising a bone graft material for emplacement in an intervertebral disc space to promote fusion of a vertebral body that is adjacent to an upper surface of the deployed expandable device to a vertebral body that is adjacent to a lower surface of the deployed expandable device.

* * * * *